United States Patent [19]
Lamb et al.

[11] Patent Number: 5,658,315
[45] Date of Patent: Aug. 19, 1997

[54] APPARATUS AND METHOD FOR LOWER LIMB TRACTION

[75] Inventors: Steve R. Lamb, Pleasanton; Allan Epstein, Los Altos Hills; Steve Orear, Hayward, all of Calif.

[73] Assignee: Orthopedic Systems, Inc., Union City, Calif.

[21] Appl. No.: 512,281

[22] Filed: Aug. 8, 1995

Related U.S. Application Data

[63] Continuation-in-part of Ser. No. 200,659, Feb. 23, 1994, abandoned.

[51] Int. Cl.$^6$ ........................................................ A61F 5/00
[52] U.S. Cl. ........................... 606/241; 606/240; 606/245; 602/32
[58] Field of Search ............................ 606/240, 241, 606/242, 245; 602/32, 34, 35, 36, 37, 39, 38, 40

[56] References Cited

U.S. PATENT DOCUMENTS

| | | | |
|---|---|---|---|
| 1,160,451 | 11/1915 | Sanford | 606/241 |
| 1,662,464 | 3/1928 | McCutchen | 602/39 |
| 2,691,979 | 10/1954 | Watson | 602/39 |
| 3,090,381 | 5/1963 | Watson | 602/39 |
| 3,745,996 | 7/1973 | Rush, Sr. | 128/84 |
| 4,730,606 | 3/1988 | Leininger | 128/75 |
| 4,866,796 | 9/1989 | Robinson et al. | 602/33 X |
| 5,088,706 | 2/1992 | Jackson | 269/232 |

OTHER PUBLICATIONS

Orthopedic Systems, Inc. Product Brochure for the Universal Orthopedic Surgical and Fracture Table.
1991 Orthopedic Systems, Inc. Product Brochure for Jackson's Spinal Surgery and Imaging Table.
Promotional materials for the AMSCO OrthoVision Orthopedic Table.
Promotional materials for the Chick–Langren Orthopedic and Surgical Operating Table Technique Manual.
Promotional materials for the Kirschner 5100 Orthopedic Table.
Promotional literature for the MIRA Ref 208 Table.
Promotional materials for the Midmark Chick 703 Orthopedic and Surgical Operating Table.
Promotional materials for the Shampaine 3700+ Table.

*Primary Examiner*—Michael Powell Buiz
*Assistant Examiner*—Kevin Truong
*Attorney, Agent, or Firm*—Limbach & Limbach LLP

[57] ABSTRACT

A lower limb traction system utilizes a perineal post for applying counter-traction and for stabilizing the patient's hips and a traction unit for supporting the leg and for maintaining traction in the leg. The traction unit is moveable along a substantially horizontal arcuate path defined by a circumferential guide and having a center of rotation that is selected to be concentric with the center of rotation location of the hip associated with the leg to be placed in traction. Abduction and adduction of a leg is achieved by moving the traction unit along the arcuate path.

28 Claims, 22 Drawing Sheets

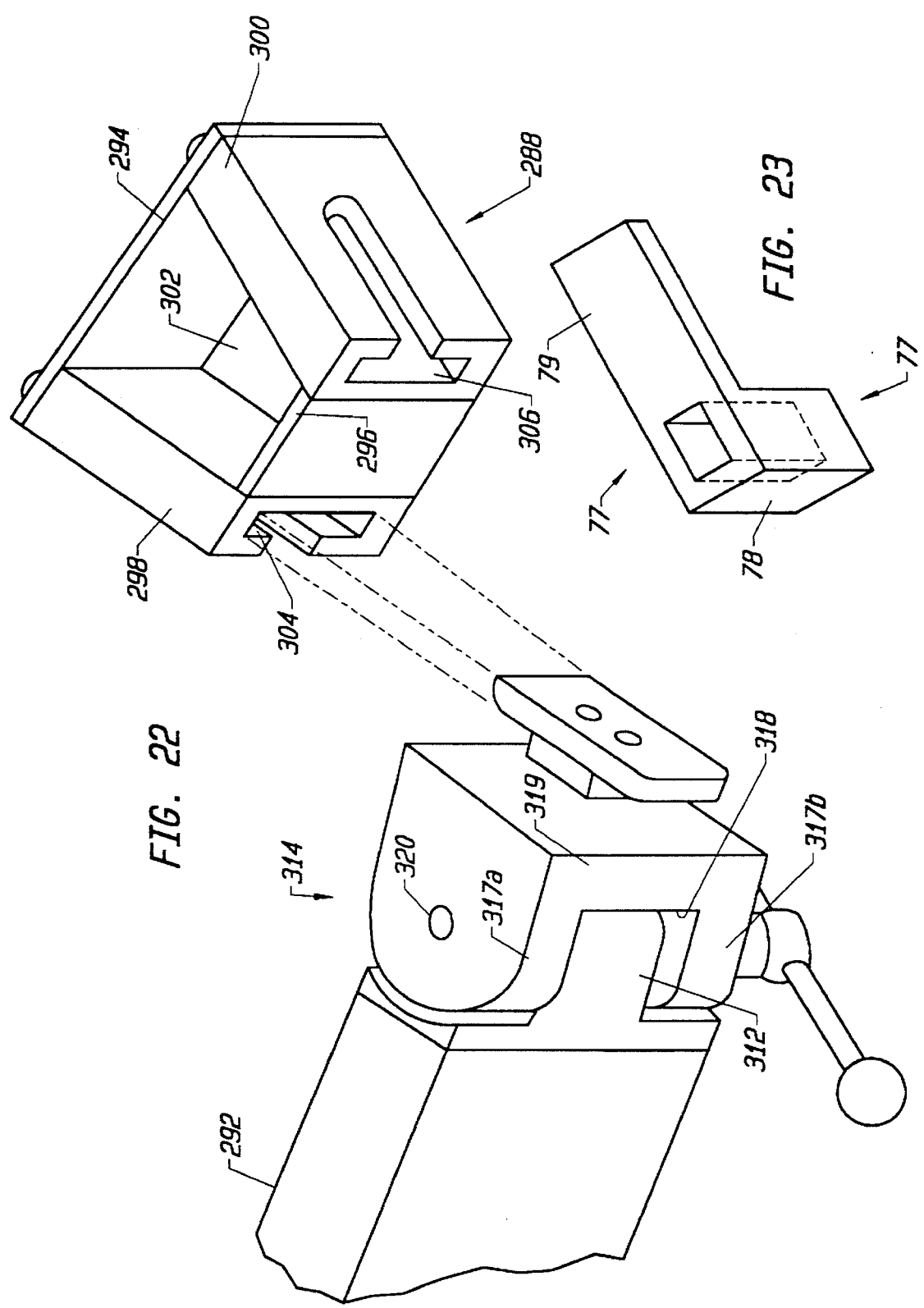

APPARATUS AND METHOD FOR LOWER LIMB TRACTION

This is a continuation-in-part of application Ser. No. 08/200,659 filed on Feb. 23, 1994 now abandoned.

FIELD OF THE INVENTION

The present invention relates to the field of orthopedic and surgical operating tables. In particular, the present invention relates to devices for placing a patient's legs in traction during orthopedic procedures.

BACKGROUND OF THE INVENTION

During orthopedic procedures, a fracture table functions to stabilize the patient and to deliver traction to one or both of the lower limbs of the patient by putting the legs in tension. In many orthopedic procedures it is necessary to abduct or adduct one or both of the legs (i.e. pivot it around its corresponding hip), while the patient is in a supine or lateral position, without relieving the traction force on the leg. Such procedures include hip pinning, casting of femoral and tibial fractures, and hip spica casting. In other procedures, such as femur nailing, it is necessary to position the patient on one side and to pivot the legs around the hips in the forward direction.

Existing orthopedic tables provide for abduction and adduction in a variety of ways. Common to many existing tables is that the patient's foot is connected to a traction unit attached to the distal end of an elongate member, with abduction and adduction being effected by pivoting the elongate member around its proximal end, which in some cases comprises a pivot point designed to approximate the location of the patient's hip. Traction units, which secure the patient's feet and which apply traction forces to the legs via the feet, are located at the distal ends of the elongate members. During use, a patient's foot is strapped into one of the traction units and he or she is positioned on a back rest with his or her hips centered along the same vertical axis as the pivot points. Abduction or adduction of the desired leg is carried out by pivoting the elongate member associated with the leg sought to be adjusted around its associated pivot point.

The location of the elongate members with respect to the patient location varies between the existing orthopedic tables. For example, in one existing table the elongate members roll along the floor of the treatment room on a system of wheels. The proximal end of each elongate member is a pivot point which is intended to be co-axial with the hip several feet above it. At the other end of the elongate member, a traction unit mounting member extends upwardly from the elongate member and supports a traction unit for holding the patient's foot. The patient's back is supported by a back rest which is mounted on a pedestal extending vertically from the floor. The proximal end of each elongate member is coupled to the pedestal. Abduction and adduction are carried out by rolling the elongate member corresponding to the leg in traction along the floor such that it pivots around its pivot point, thereby carrying the leg around the pivot point.

In another table, the back rest which holds the patient is mounted to a pedestal rising vertically from the floor. The elongate members (commonly referred to as "spars") are coupled to the pedestal at the distal end of the back rest, just below the back rest, and extend cantilever-style from the pedestal. The traction units are coupled to the distal ends of the spars.

In a third type of existing orthopedic table, the elongate members are incorporated into a large framework positioned over the patient. The framework is a large structure supported by four posts extending vertically from the floor to frame a rectangular box around the patient. As with the first two units, the elongate members are substantially parallel to the location of the patient's legs, but in this type of table the elongate members are several feet above the patient. The traction units hang from a pair of substantially vertical members extending downwardly from the elongate members.

While each of the existing orthopedic tables described is effective for maintaining traction and for enabling abduction and adduction, these tables present difficulties when image intensification is used during the orthopedic procedure. An image intensification unit is comprised of an x-ray transmitter and an x-ray receiver positioned at the top and bottom, respectively, of a large C-shaped member. To use an image intensifier, the C-shaped member is positioned around the limb sought to be imaged. X-rays are directed at the limb by the x-ray transmitter and are received by the x-ray receiver. Image intensification units are mounted on a base having wheels so that the units may be rolled up to the patient for imaging and then rolled out of the way to allow the orthopedic procedure to proceed.

The first of the existing orthopedic tables described above presents difficulties with the use of an image intensifier in that when the patient's limbs are abducted, one or both of the elongate members extend broadly across the floor. The elongate members thus make it difficult to roll an image intensifier into position for imaging, since the base of the image intensifier can collide with the elongate members.

The second of the existing orthopedic tables described above also presents problems with respect to image intensification in that the spars are positioned so close to the patient's legs that they are within the imaging field. These spars, even when constructed from materials such as radiolucent carbon fiber, are not completely penetrable by x-rays. The x-ray images produced can therefore include images of the spars which are superimposed on the images of the legs and which therefore prevent clear images of the bones of the legs.

Although the third type of existing orthopedic table described above keeps the imaging area substantially free from hardware that can obstruct the imaging field or present obstacles to the positioning of the image intensifier within the imaging field, its extensive frame system renders it cumbersome, difficult to store, and highly immobile.

Moreover, because each of the above-described designs relies on a cumbersome system of members for affecting abduction and adduction, these leg traction systems are normally configured to be used only on a specific type of orthopedic table.

Also inherent with the first and second table designs is the problem of possible loss of traction during abduction and adduction. During abduction and adduction, the leg being moved must move along the arc of a circle having a center co-axial with the location of the patient's hip, since the hip is the natural pivot point of the leg. If movement is not centered around the axis of the hip, the distance between the patient's hip and foot will be forced to change to accommodate rotation about the hip and will thereby cause increases and decreases in tension in the leg as the leg is abducted or adducted.

Table designs of the first and second type are sometimes problematic in that they often do not adequately align the pivot point of the elongate member with the hip location. These table designs utilize a single pedestal, which must be positioned to balance the patient's weight. Since the patient's center of mass is in the lower back region, the pedestals on these tables are located near the sacral region of the back. Because the pedestals are located at the sacral region, there is no room there for the pivot points of the elongate members. The pivots points are thus shifted from the proper hip location, thereby causing increase in and loss of traction during abduction and adduction.

The pedestal employed in the first and second table designs also limits the versatility of the tables. Patients requiring lower limb traction are often the victims of accidents in which multiple injuries have been sustained. During treatment of such patients it is desirable to obtain x-ray images of various regions of the body, such as the torso and upper limbs, without removing the patient from traction. Because the pedestals utilized in these tables are configured to balance and support the patient's weight, they extend fairly broadly beneath the back rest and thus prevent access to the upper body by the C-shaped image intensification unit.

OBJECTS AND SUMMARY OF THE INVENTION

It is an object of the present invention to provide a system for applying traction to the lower limbs of a human patient during orthopedic procedures. It is another object of the present invention to provide a traction system having abduction and adduction capabilities. Another object of the present invention is to provide a traction system capable of abduction and adduction of a patient's leg without loss of traction. Still another object of the present invention is to provide a traction system that may be adapted for use with a variety of trauma, general surgical, orthopedic, or other medical table designs.

Other objects of the present invention relate to its use during x-ray imaging procedures. One such object is to provide a table which will allow access to the lower limbs by an image intensifier unit and which will provide an imaging field which is substantially free from hardware that may obstruct the imaging field. Another such object is to provide a traction table which may also be used during imaging of a patient's torso and upper body.

It will be shown that these objects and others are achieved by the traction system of the present invention.

The lower limb traction device of the present invention is configured for use with an orthopedic or surgical table. The traction system is comprised of a traction device, such as a foot traction unit, for supporting the distal portion of the leg in a desired traction position. A stabilizing means, such as a perineal post, provides counter-traction and maintains positioning of the patient's hips such that the center of rotation of the hip associated with the leg to be placed in traction is in a hip location. A circumferential guide that is remote from the hip location defines an arcuate path having a center located at the hip location. The traction device is moveable along the arcuate path to position the leg at a desired angle from the longitudinal axis of the patient's body.

DESCRIPTION OF THE DRAWINGS

FIG. 22 is a perspective view of the coupling mechanism for the supplemental traction spar of FIG. 21.

FIG. 23 is a perspective view of a casting saddle according to the present invention.

DETAILED DESCRIPTION OF THE PREFERRED EMBODIMENT

Figure 1:
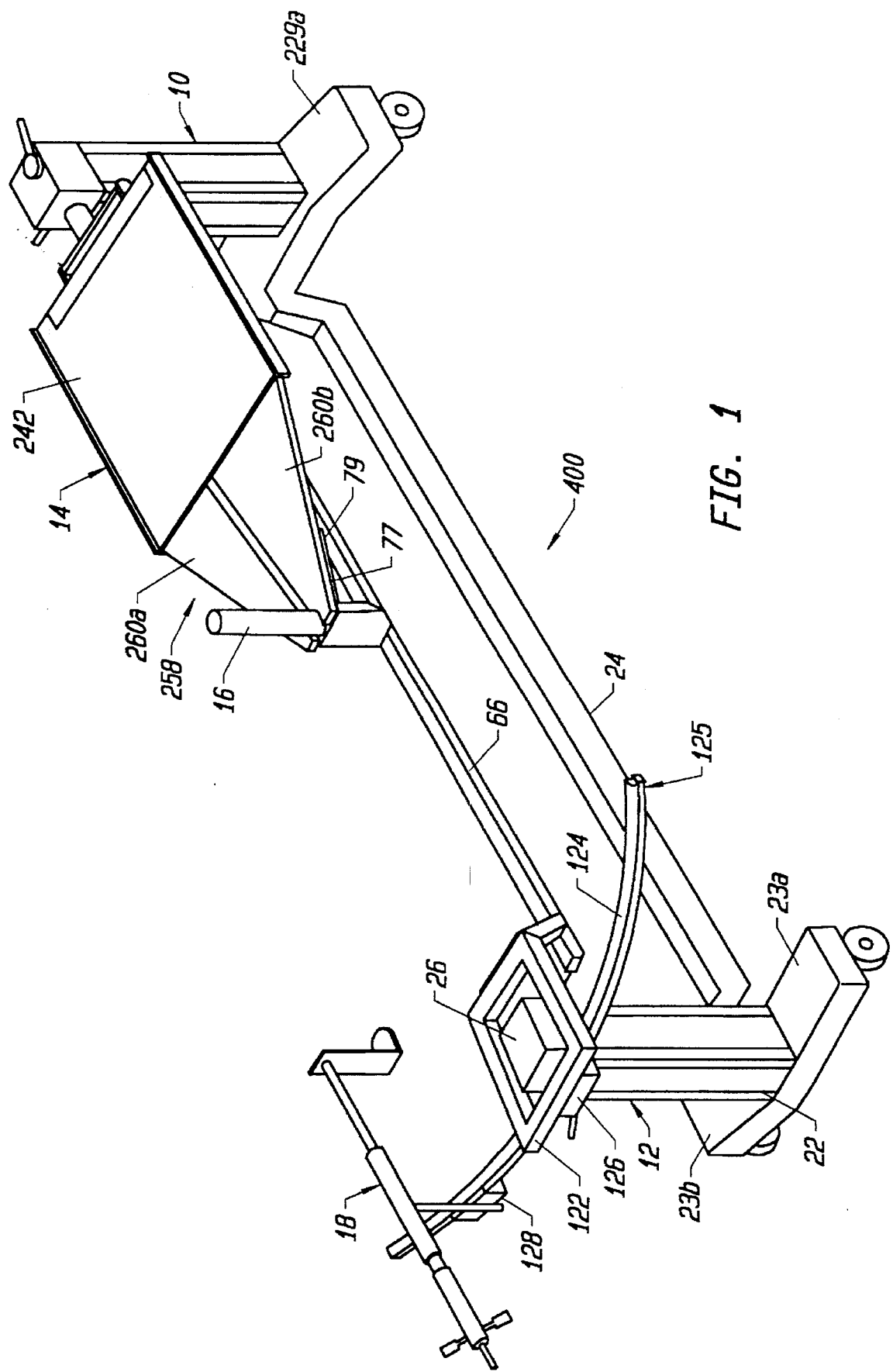
FIG. 1 is a perspective view of an orthopedic table equipped with the traction unit of the present invention.

The table 400 of the present invention is comprised generally of a head post 10, a foot post 12 and a patient support unit 14 extending between them. A perineal post 16 extends normally of the patient support unit 14. A traction unit 18 is positioned near the foot post 12. Placing a patient's leg in traction requires putting the patient into a traction position whereby the patient is positioned on the table with the perineal post 16 positioned between its legs and with its foot secured to the traction unit 18. Traction is provided by applying a traction force to the leg via the traction unit 18.

Figure 2:
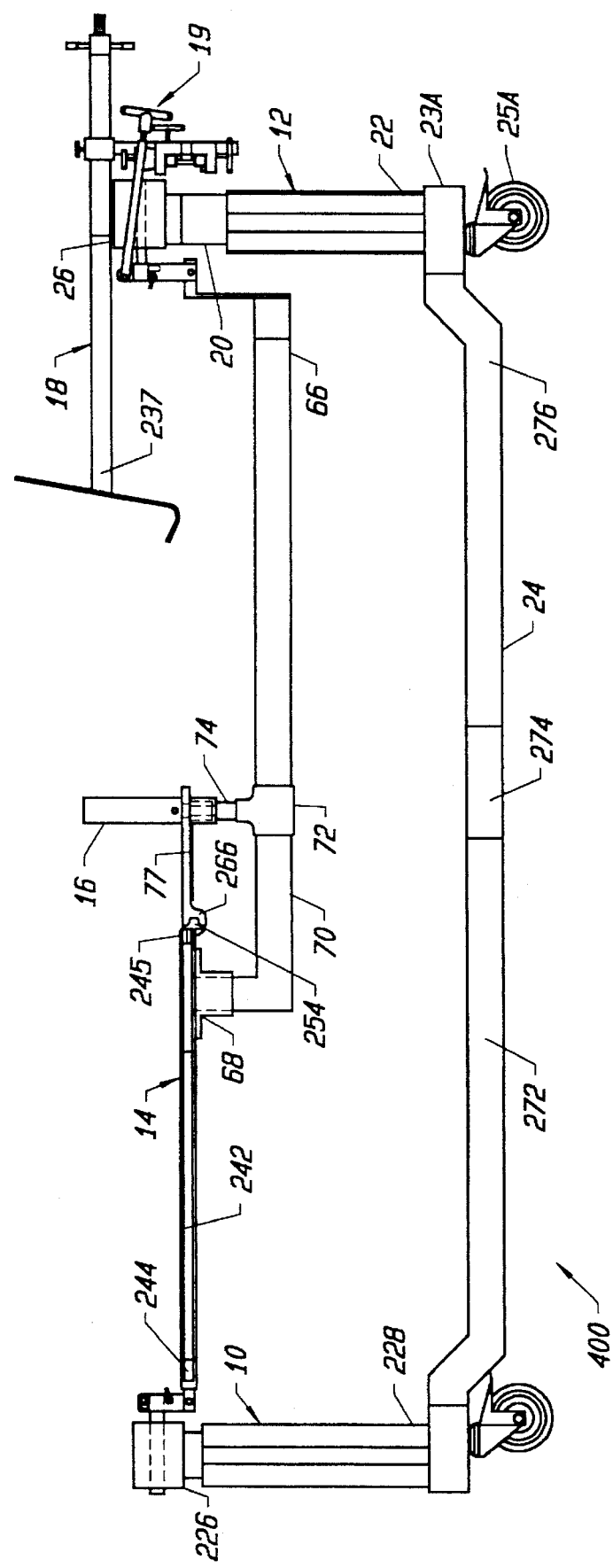
FIG. 2 is a side elevation view of the orthopedic table of FIG. 1.
Figure 3:
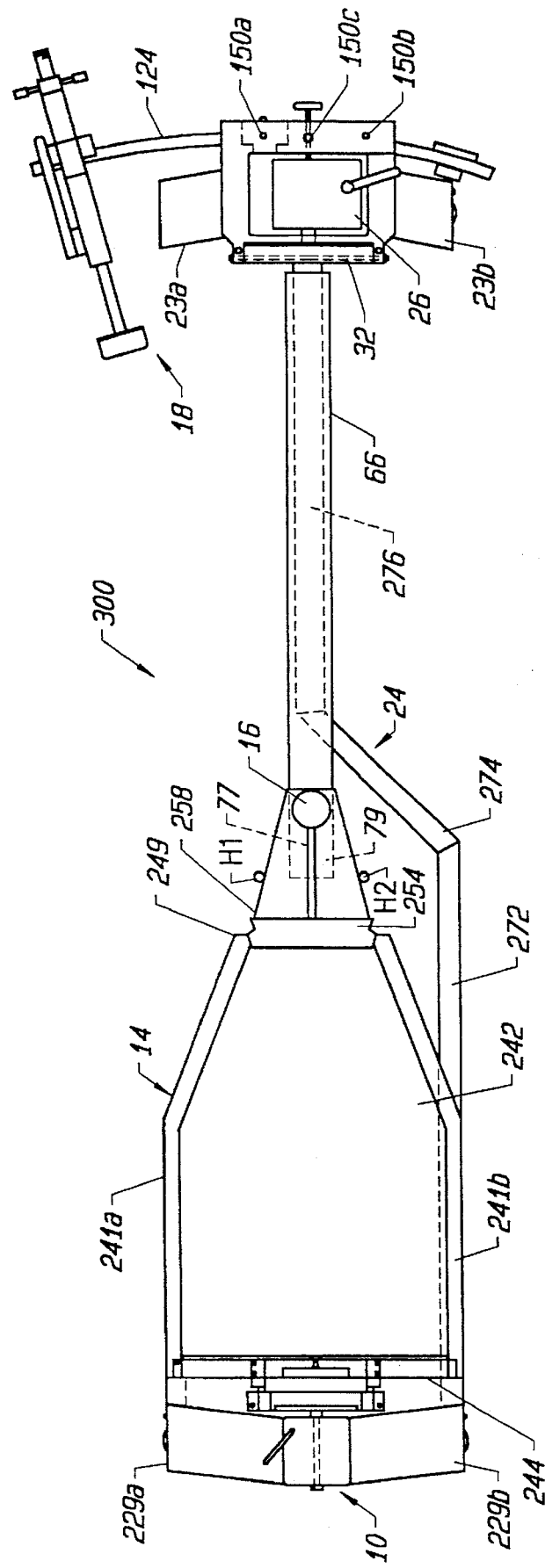
FIG. 3 is a top plan view of the orthopedic table of FIG. 1.

Referring to FIGS. 2 and 3, foot post 12 is an elongate post having a top section 20 and a bottom section 22. The bottom section 22 is fixed to the base beam 24. Two wheel bases 23a, 23b extend laterally from the bottom section 22. Wheels 25a, 25b are connected to the wheel bases and serve to support the weight of the table and to allow the table to be rolled across a floor. The wheels 25a, 25b may be provided with locks (not shown) which prevent the table from rolling except when the locks are released.

Figure 4:
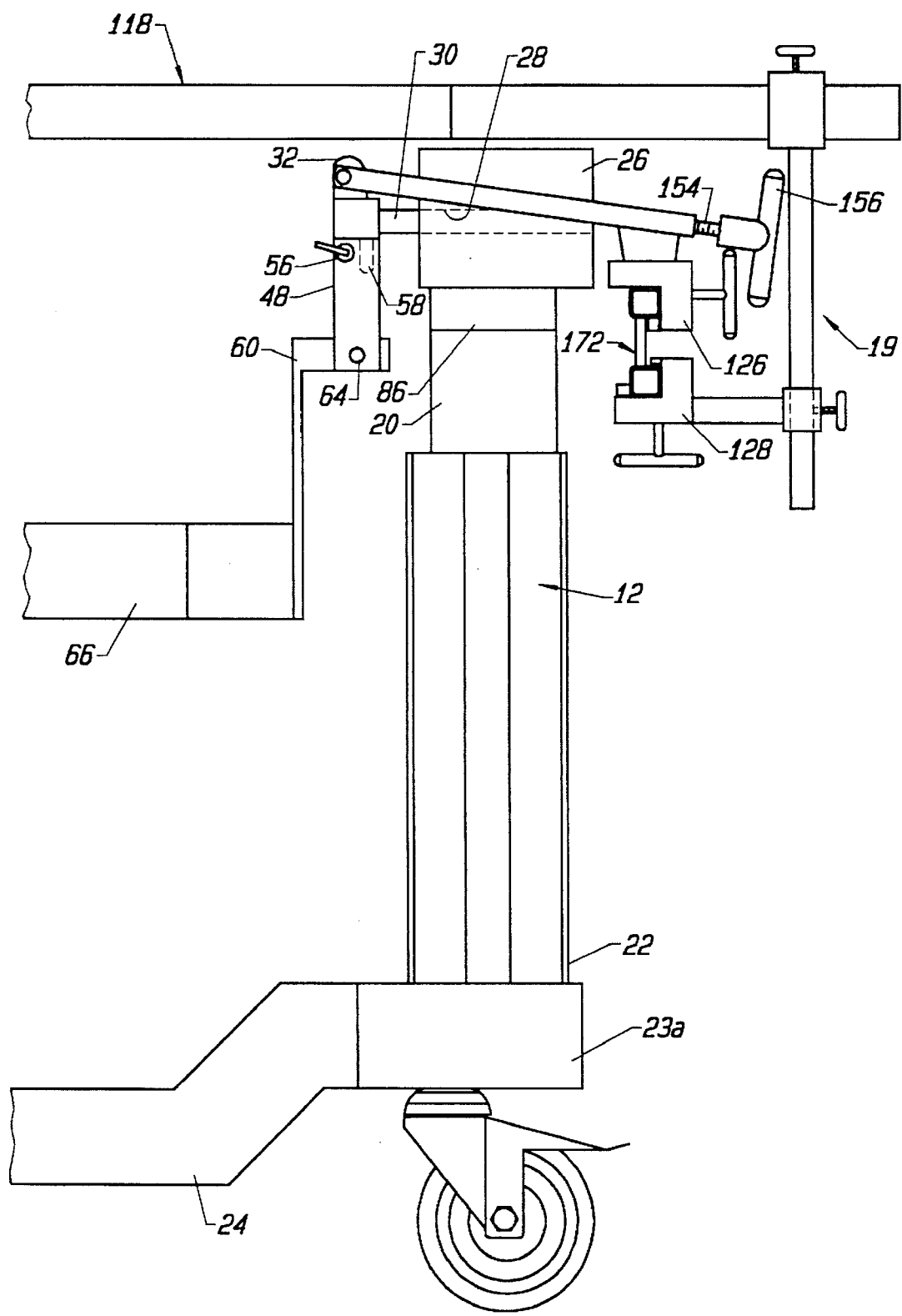
FIG. 4 is a side elevation view of the distal end of the orthopedic table of FIG. 1.
Figure 5:
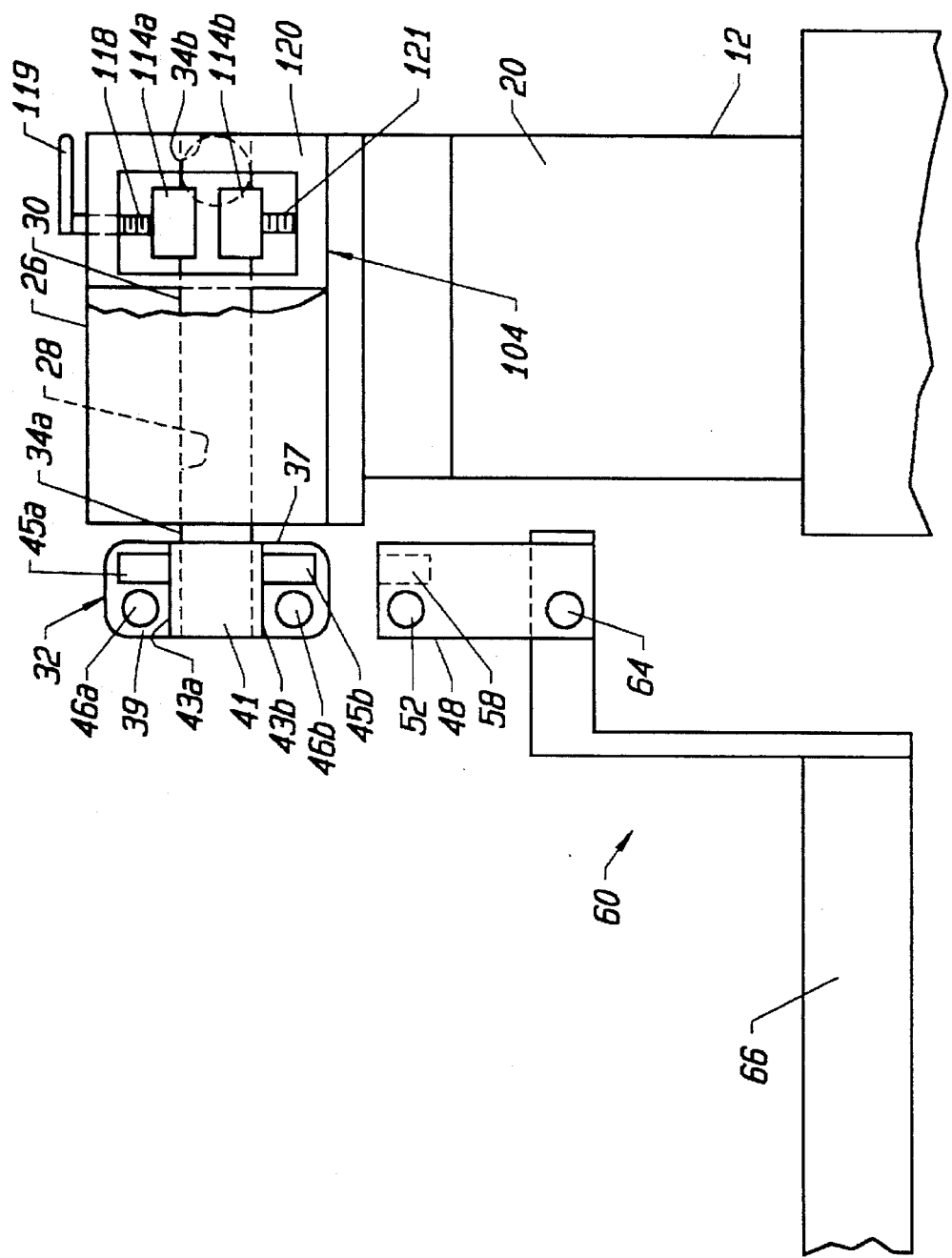
FIG. 5 is a partial side elevation view of the upper portion of the foot post of the table of FIG. 1 with the table spar detached from the cross member and with the traction system not shown.
Figure 6:
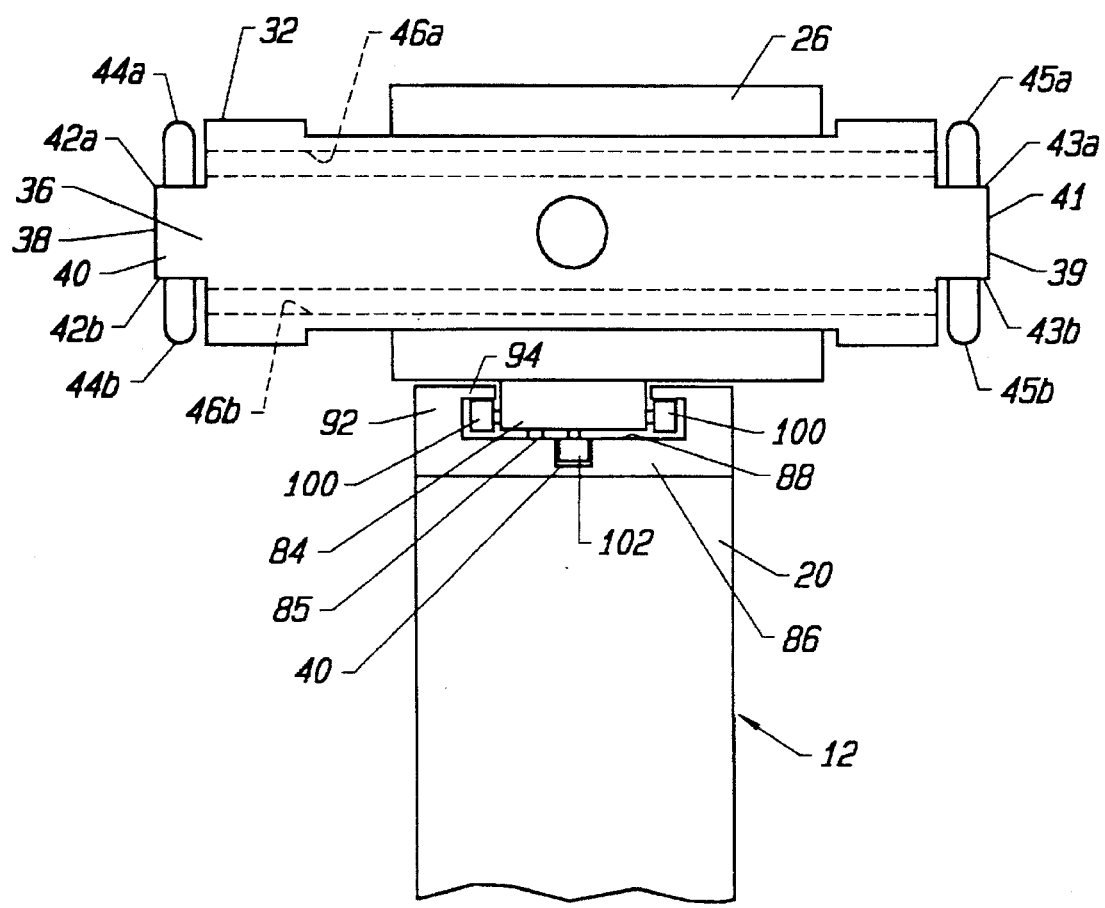
FIG. 6 is a front elevation view of the upper portion of the foot post with the traction system not shown.

The components associated with the foot post 12 may be seen in greater detail in FIGS. 4–6. The top section 20 is slidable within the bottom section 22 to raise or lower the height of the distal end of the table. An electric motor, hydraulic pump, or other means (not shown) for raising and lowering the top section 20 relative to the bottom section 22 is located inside the bottom section 22.

Connected to the top section 20 is a housing 26 which, as will be discussed below, houses a foot brake unit. A throughbore 28 having a longitudinal axis that is parallel to longitudinal axis of the table passes through the housing 26, and a shaft 30 is rotatably disposed within the throughbore 28. A cross member 32 is fixed to one end 34a of the shaft 30 such that the longitudinal axis of the shaft 30 passes through the center of the cross member. The other end 34b of the shaft is housed inside the housing 26.

The cross member 32 is an elongate member having a pair of elongate faces 36, 37 and two ends 38, 39. Ribs 40, 41 extend laterally from the ends 38, 39, respectively, of the cross member 32. Each rib 40, 41 has a pair of parallel faces, designated 42a, 42b and 43a, 43b, respectively.

Mounted to each of the faces 42a, 42b of the rib 40 is an elongate finger 44a, 44b. Identical fingers 45a, 45b are mounted to the faces 43a, 43b of rib 41. Adjacent to each finger 44a, 44b is a throughbore 46a, 46b which extends the entire length of the elongate member, parallel to the longitudinal axes of the elongate faces 36. The cross member 32 is fixed to the shaft 30 such that the longitudinal axis of the shaft is normal to and centered on the faces 36.

A pair of parallel connectors 48, 50, (connector 50 and its components are obscured by connector 48 in the drawings) each provided with a hole 52, 54, are suspended from the ends 38, 39 of the cross member 32 such that bore 46b (FIG. 5) of the cross member is positioned between the holes 52, 54 on the connectors 48, 50. A rod 56 (see FIG. 4) extends through hole 52, bore 46b, and hole 54 to fix the elongate members 48, 50 to the cross member 32. A locking device (not shown) is provided to prevent the rod 56 from accidentally sliding out of place and releasing the elongate members from the cross member. Each connector 48, 50 has a vertically oriented bore 58 which receives one of the lower fingers 44b, 45b on the cross member 32.

Figure 7:
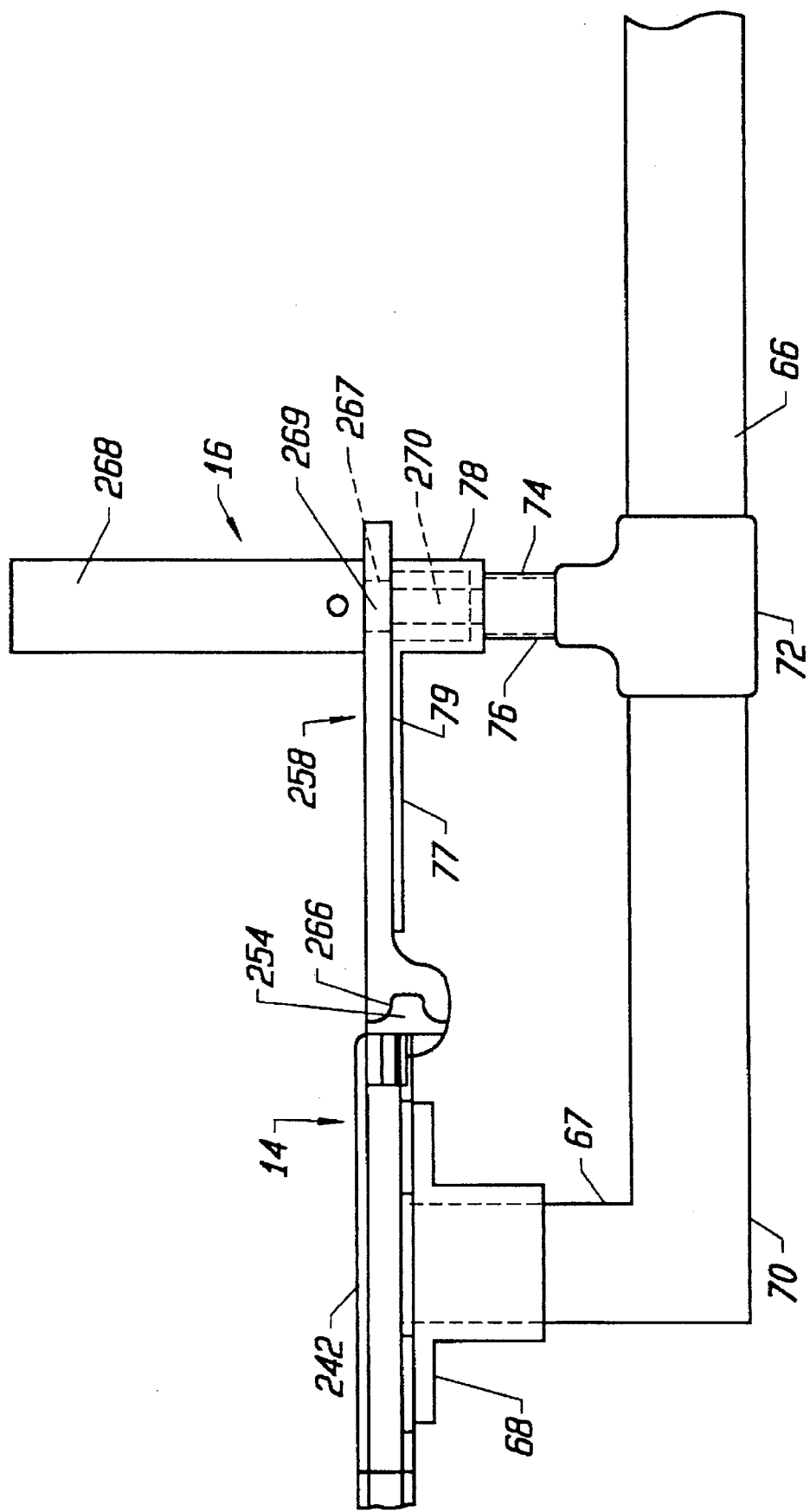
FIG. 7 is a partial side elevation of the table of FIG. 1.

Pivotally joined to the connectors 48, 50 at pivot point 64 is a bracket 60. A table spar 66 is fixed to the bracket 60 and extends longitudinally towards the head post 10. As shown in FIGS. 2 and 7, the spar 66 has a vertical portion 67 at its proximalmost end 70 which is joined to the patient support unit 14 by connector 68. The longitudinal axis of the spar 66 shares a vertical plane with the longitudinal axis of the shaft 30 (FIG. 4) and the table 400 (FIG. 1).

The spar 66 is preferably formed from a material, such as carbon fiber, which has good radiolucent properties. The shape of the spar may also be designed to optimize its radiolucency. As previously described, when image intensification is used to image a patient's leg, the x-rays are emitted on one side of the leg to be imaged and received on the other side of the leg. It is therefore preferable to minimize the thickness of any extraneous objects within the imaging field in order to minimize the shadows those objects cause on the image.

Figure 8:
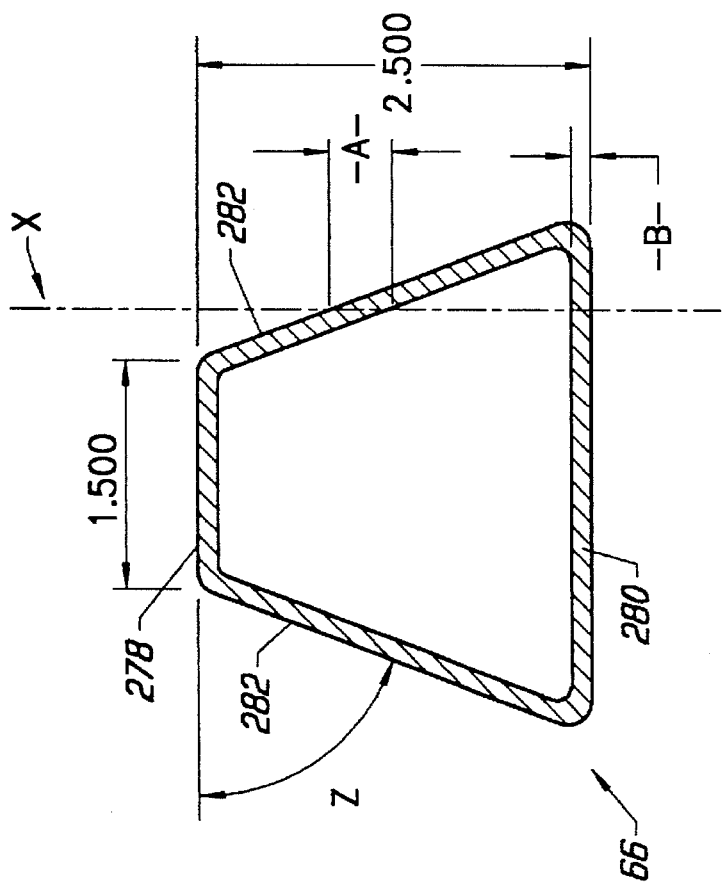
FIG. 8 is a cross-section view of the preferred table spar according to the present invention.

FIG. 8 shows the preferred cross section for the table spar 66. The trapezoidal shape of the preferred spar increases its radiolucency because the maximum aggregate thickness of the spar material within the imaging field is much smaller than it is for spars having rectangular cross sections. By reducing the maximum aggregate thickness of the spar material, the appearance of shadows in the x-ray images is thereby minimized The spar 66 is comprised of four walls, all of which extend for the entire length of the spar. First wall 278 and second wall 280 are positioned in spaced parallel relation. First wall 278 is shorter than second wall 280 and is positioned above it. Third walls 282 are equal in length and connect the first and second walls to form a trapezoidal cross-section. The angle Z between the plane of the first wall 278 and each of the third walls 282 is preferably 70°. When x-rays are directed towards the spar 66 at right angles to the parallel walls 278, 280, the maximum aggregate thickness of spar material that would be encountered by the x-rays would lie along the plane designated X in FIG. 8. That thickness may be represented as A+B, where A is the thickness of third wall 282 taken along plane X and B is the thickness of the second wall 280. In its preferred form, the spar has a maximum thickness, A+B, of less than 0.625 inches.

Figure 10:
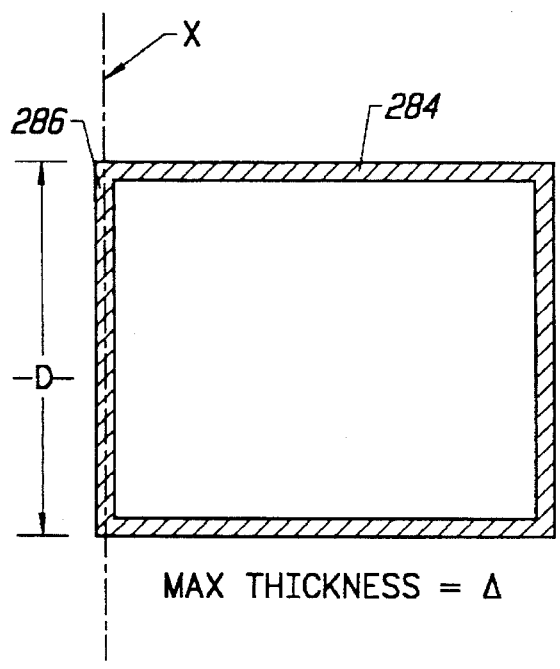
FIG. 10 is a cross-section view of a prior art table spar.

For purposes of contrast, a cross-section of a prior art table spar is shown in FIG. 10. The prior art spar is comprised of a rectangle having first walls 284 and second walls 286. As can be seen, x-rays directed towards the prior art spar would be required to pass through a maximum thickness equal to the length D of one of the second walls 286.

Figure 9:
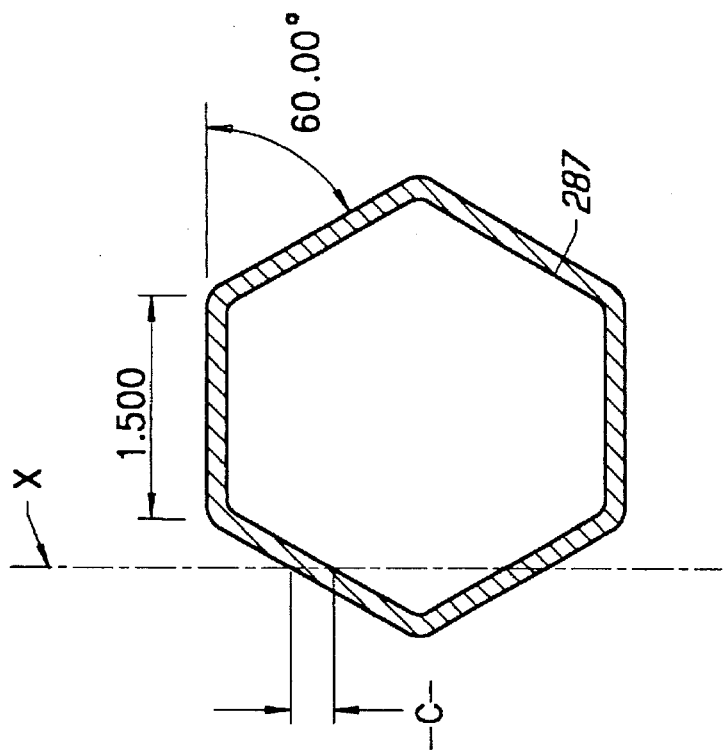
FIG. 9 is a cross-section view of an alternate table spar according to the present invention.

As will be appreciated in light of the preceding discussion, alternative spar cross sections, such as the one shown in FIG. 9, may also be used to minimize x-ray shadowing. The alternative cross section of FIG. 9 is comprised of six sides 287 of equal length.

As can be seen in FIG. 7, a sleeve 72 is disposed around the table spar 66 near the proximal end 70 of the spar. The sleeve supports a rectangular column 74 which extends normally of the table spar 66 and which has a square cross-section. The column has a bore 76 with a rectangular cross section passing through it in the vertical direction.

A casting saddle 77 may be provided for use in the application of hip spica casts. The casting saddle, which can be seen in top view in FIG. 3 and in perspective view in FIG. 23, is comprised of a rectangular plate 79 extending from a rectangular sleeve 78. The sleeve 78 is disposed around the rectangular column 74 (FIG. 7) such that the casting saddle 77 is positioned directly below the sacral rest 258. The casting saddle 77 must be provided with sufficient strength and rigidity to support the weight of the patient during casting.

Figure 12A:
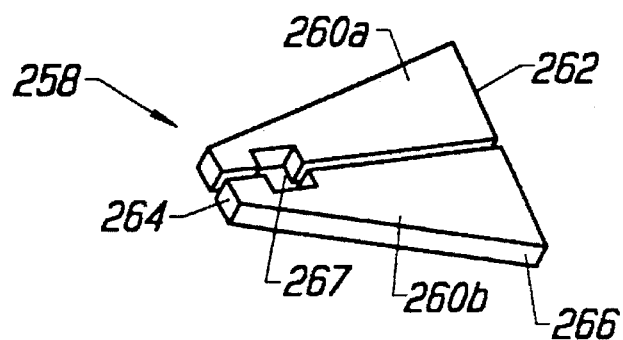
FIG. 12A is a supinal sacral rest of the orthopedic table of FIG. 1.

A supinal sacral rest 258 is comprised of two identical boards 260a, 260b (FIG. 12A) which, when assembled, form a trapezoid having a long proximal end 262 and a shorter distal end 264 that are parallel to each other. A square cutout 267 is formed near the distal end 264 of the sacral rest 258.

The proximal end 262 of the supinal sacral rest 258 is formed into a dovetail receiver 266 which, as shown in FIG.

7, is configured for lateral sliding engagement with dovetail connector 254 on back board 242.

Figure 11:
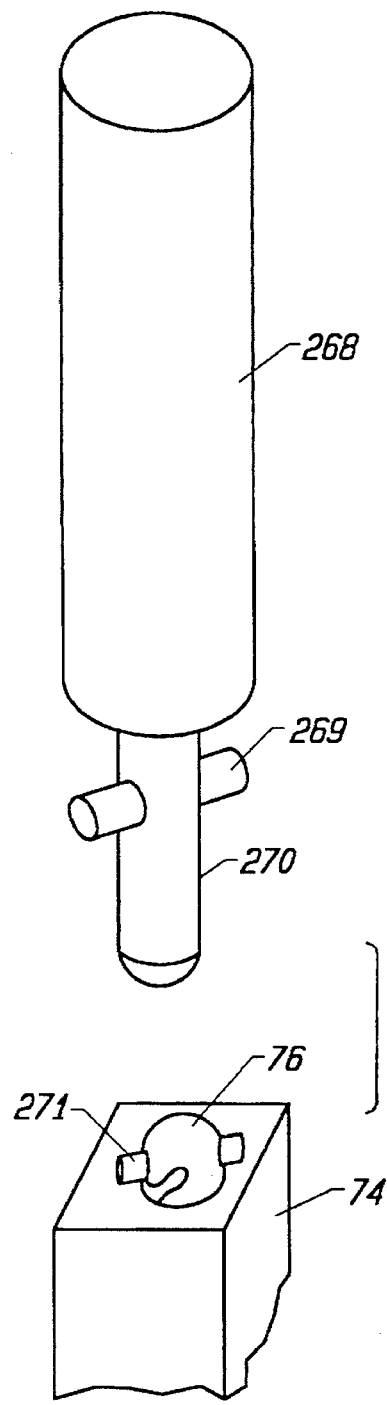
FIG. 11 is a perspective views of a conventional perineal posts used for supinal procedures.

The perineal post 16 may be one of a variety of types of perineal posts conventionally used for countertraction. A perineal post 16 of the type used with the supinal sacral rest is shown in FIG. 11A. It is comprised of a cylindrical member 268 covered in a soft padding, such as padded vinyl, and an elongate post 270 which extends longitudinally from the cylindrical member 268. The perineal post 16 is positioned with the elongate post 270 extending through the cutout 267 of the sacral rest 258 and into the bore 76 in the column 74 and may be secured there by conventional means. For example, as shown in FIG. 11A, the elongate post 270 may be provided with a pair of pegs 269 extending laterally from the elongate post 270 in opposite directions, and the bore 76 in the column 74 may be provided with a pair of notches 271 for receiving the pegs 269. The bore 76 may additionally be provided with a pair of grooves (not shown) each of which is contiguous with one of the notches such that after the post 270 is inserted into the bore 76 it may be rotated 90° such that the pegs 269 travel within the grooves to prevent the perineal post 16 from lifting out of place during traction procedures.

Figure 12B:
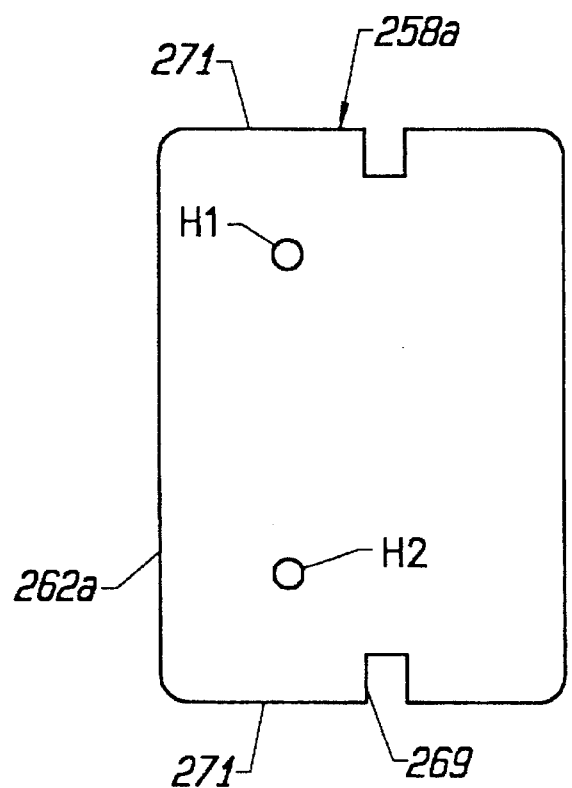
FIG. 12B is a lateral sacral rest of the orthopedic table of FIG. 1.

The table according to the present invention may also be provided with a lateral sacral rest 258a such as the one shown in FIG. 12B. This type of sacral rest is necessary during procedures, such as intramedullary nailing of the femur or tibia, in which the patient must be positioned on one of his or her sides. The lateral sacral rest has a proximal end 262a which, like the proximal end 262 of the supinal sacral rest 258, is formed into a dovetail receiver (not shown in FIG. 12B). A pair of rectangular cutouts 269 are formed along the sides 271 of the sacral rest 258a.

For lateral procedures, a perineal post which is similar to perheal post 16 but which has a second post, called a lateral pad extending laterally from the cylindrical column 268. During use the lateral perineal post is normally fixed to the sacral rest at one of the cutouts 269 and the lateral pad is positioned in the perineal region of the patient. As with conventional traction tables, the perineal post must be securely engaged with the sacral rest 258a or another portion of the table in order to lock it against rotational movement during use.

The foot brake housing 26 is associated with two general components: a sliding component which permits longitudinal sliding of the patient support unit and a locking component which, when utilized, locks the patient support unit against rotation.

Figure 13:
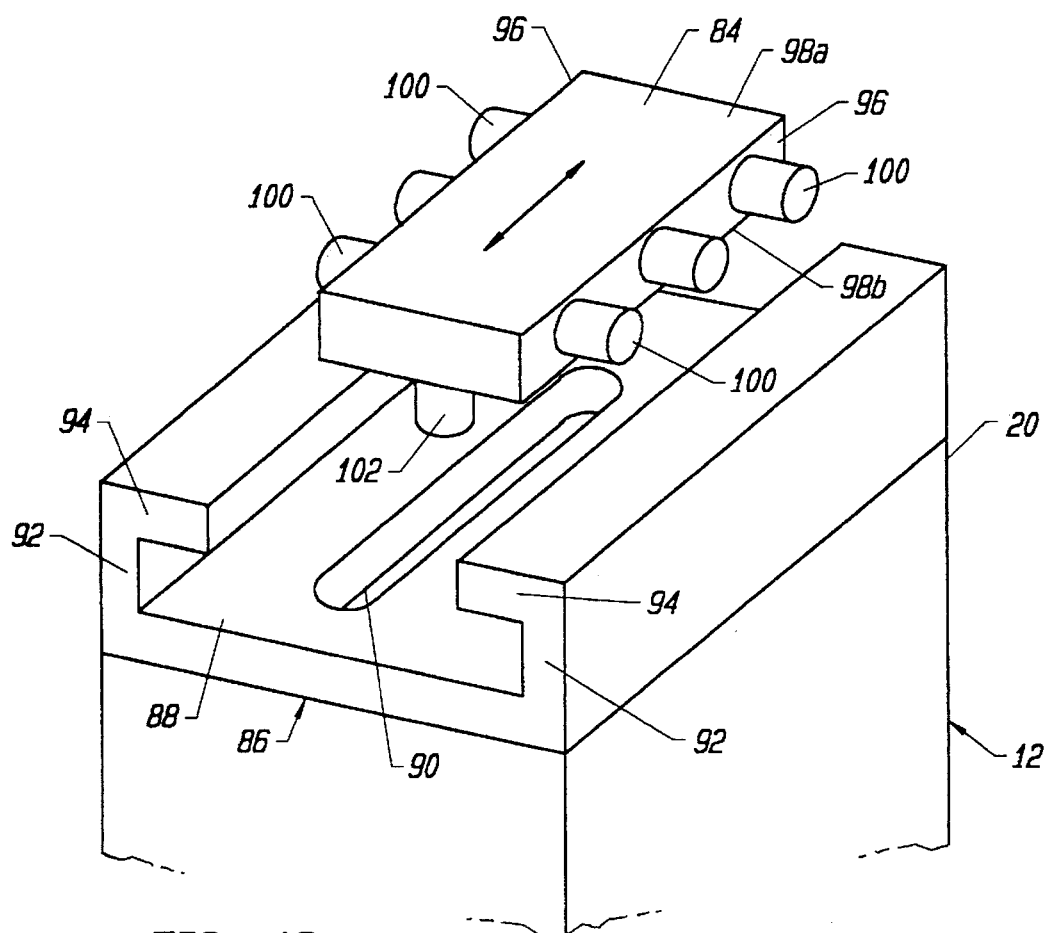
FIG. 13 is a perspective view of a trolley system mounted to the top of the foot post of the orthopedic table of FIG. 1.

The sliding component is shown in FIG. 13. It is comprised of a trolley 84 which is fixed to the housing 26 (not shown in FIG. 13) and which is slidable along a base 86 that is fixed to the top end 20 of the foot post 12.

The base 86 is comprised of a rectangular plate 88 having a slot 90 extending in the longitudinal direction. A pair of parallel walls 92, which are also parallel to the slot 90, extend normally of the plate 88. A second pair of walls 94 extend normally of the walls 92 in a laterally inward direction.

The trolley 84 is a rectangular block having a pair of long faces 96 and top and bottom faces designated 98a and 98b, respectively. Needle bearing rollers 100 extend laterally from each of the long faces 96 and another needle bearing roller 102 extends downwardly from the bottom face 98b of the trolley 84.

The top face 98a of the trolley 84 is connected to the housing 26. As shown in FIG. 6, the trolley 84 is slidably mounted to the base 86 such that the rollers 100 are disposed between the plate 88 and the walls 94. The roller 102 is slidable within the slot 90 in the plate 88. The trolley 84 is thus able to roll along the plate 88 in the longitudinal direction as indicated by arrows in FIG. 13. Because the cross member 32, elongate members 48, 50, and table spar 66 are coupled to the housing 26 by virtue of the shaft 30, sliding movement of the housing 26 along the plate 88 results in longitudinal movement of the patient support unit 14. Rolling resistance may be increased or decreased by means of a piece of friction material 85 (FIG. 6) connected to trolley 84 by a set screw which may be adjusted to increase or decrease pressure imposed on the base 86.

Inside the foot brake housing 26 is a braking device 104 which is designed to engage the shaft 30 and to thereby prevent rotation of the shaft 30 when it is desired to prevent rotation of the patient support unit 14.

Figure 14:
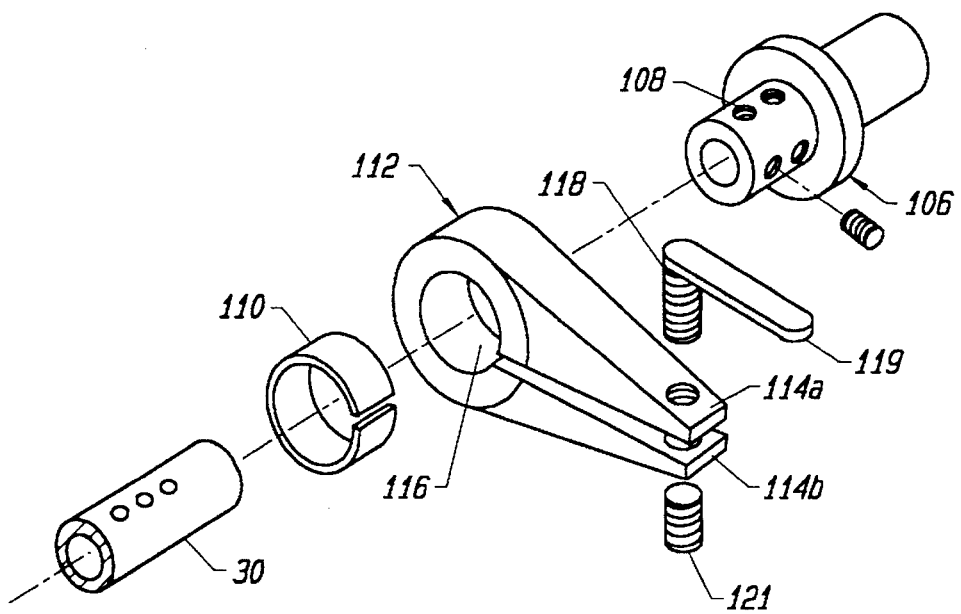
FIG. 14 is an exploded perspective view of the rotational braking system of the orthopedic table of FIG. 1.

As shown in the exploded view of FIG. 14, the braking device 104 is comprised of a brake drum 106 which is connected to the shaft 30 by a series of set screws 108. A brake liner 110, formed of brass or other friction material, is positioned around the brake drum 106. A brake clamp 112 having a pair of clamping members 114a, 114b and a bore 116 is disposed around the brake liner such that the brake liner and drum are positioned within the bore. Referring to FIG. 5, the clamping members are positioned inside a rectangular block 120. A threaded brake lock 118 (FIG. 5 and 14) passes through a threaded bore in block 120 such that when handle 119 is tightened, the brake lock presses member 114a of brake clamp 112 towards member 114b to compress brake drum 106 and to thereby prevent rotation of the shaft 30. Threaded brake adjustor 121 is positioned in abutting engagement with clamping member 114b and may be advanced or withdrawn to adjust braking resistance.

No mechanism is provided for locking the trolley 84 (FIG. 13) against sliding movement. This is unlike conventional braking systems which simultaneously prevent both rotation and longitudinal movement of the table. Although it is normally desirable to lock the table against rotation when a patient is in traction, it is essential in the present system to allow longitudinal movement to occur. This is because adjustments may be made to the table which may alter the longitudinal length of the patient support unit 14 while the distance between the head post 10 and the foot post 12 remains constant. For example, the proximal end 244 of back board 242 (which is described in detail below) may be elevated while the height of the table spar 66 is left unchanged. This adjustment would decrease the longitudinal length of the patient support unit 14 because the adjustment would cause what had been the head-to-foot length of the patient support unit 14 to become the hypotenuse of a right triangle. The patient support unit 14 must be able to respond to such an adjustment by longitudinal sliding or it will become spring loaded, a condition which should be avoided particularly during surgical procedures.

Figure 15:
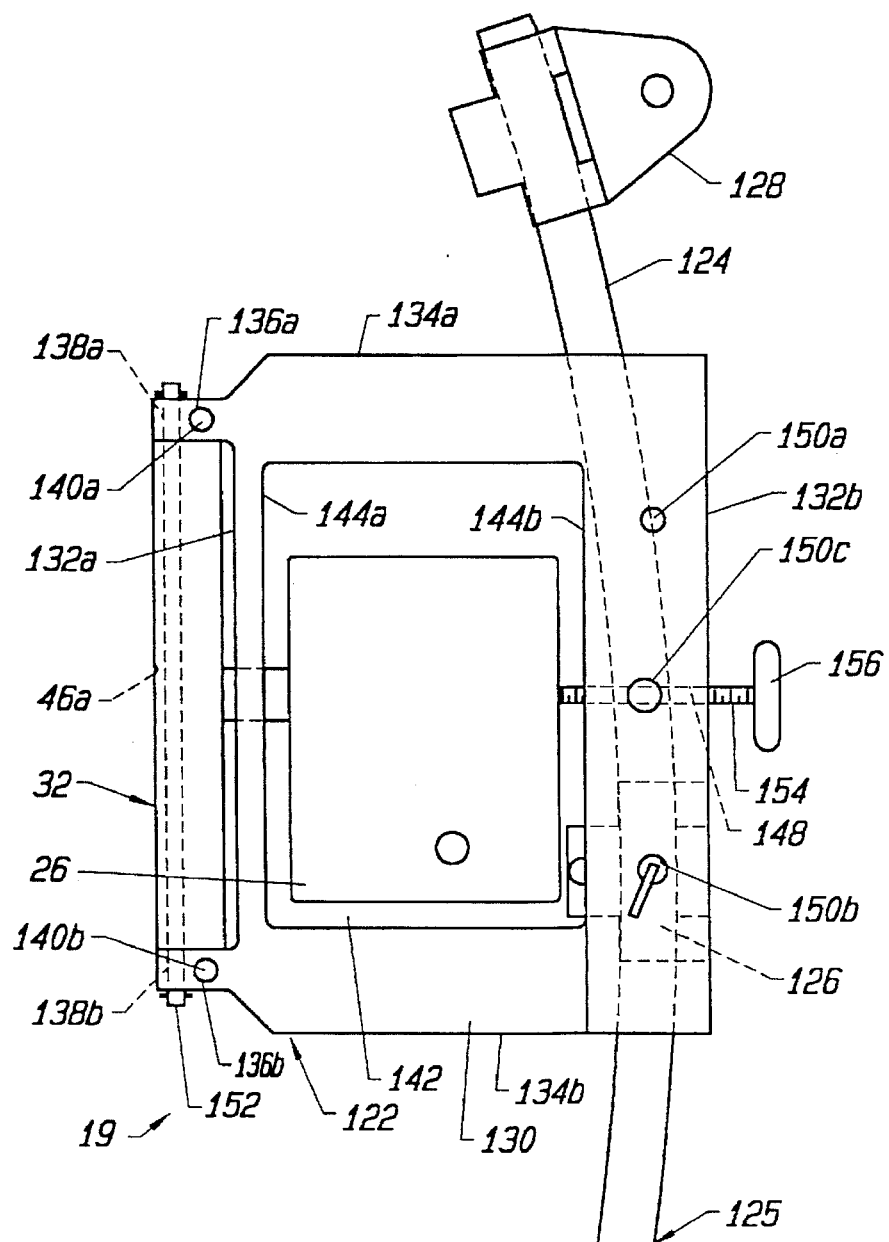
FIG. 15 is a top plan view of the traction system according to the present invention.

As shown in FIG. 4, the traction unit 18 is coupled to a traction system 19 which is designed to be adaptable for use on a variety of tables including trauma tables, general surgical tables, and orthopedic tables. Referring to FIG. 15, the traction system 19 as configured for use on tables of the type shown in the accompanying drawings is comprised generally of a base member 122, a circumferential guide 125, a base trolley 126 for positioning the circumferential guide 125 relative to the base member 122 and a pair of traction trolleys 128 for positioning the traction unit 18 (not shown in FIG. 15) along the arcuate path defined by the circumferential guide. During use, the traction unit 18 is connected to one of the traction trolleys 128, depending on which leg is to be placed in traction. Together the base trolley 126 and the traction trolleys 128 serve to position the traction unit 18 to provide the desired degree of traction and abduction to a leg secured to the traction unit 18.

The base member 122 is comprised of a substantially rectangular plate 130 having a pair of long sides 132a, 132b and a pair of short sides 134a, 134b. Extending laterally from long side 132a is a pair of tabs 136a, 136b. Each tab 136a, 136b has a first bore 138a, 138b formed in it. Bores 138a and 138b share a common longitudinal axis which is substantially parallel to the long sides 132a, 132b of the rectangular plate 130. Each tab 136a, 136b has a second bore 140a, 140b passing through it in a direction normal to the plane of the tab. The second bores 140a, 140b are proportioned to receive the upper elongate fingers 44a, 45a (see FIG. 6) of the cross member 32.

The rectangular plate 130 has a rectangular cutout section 142 having long sides 144a, 144b that are substantially parallel to the long sides 132a, 132b of the rectangular plate 130. A threaded throughbore 148 is centered between short sides 134a, 134b of the rectangular plate 130 and extends from long side 132b of the rectangular plate to long side 144b of the cutout section 142. Bores 150a, 150b, and 150c are positioned on opposite sides of throughbore 148 at equal distances therefrom. The longitudinal axes of the bores 150a, 150b, and 150c are parallel to the longitudinal axes of the second bores 140a, 140b.

A rod 152 connects the rectangular plate to the cross member 32. The rod 152 extends through the bores 138a, 138b on the tabs 136a, 136b of the base member 122 and through the throughbore 46a of the cross member 32. The rod is provided with a locking mechanism (not shown) which prevents the rod 152 from inadvertently falling out of the bores.

The foot brake housing 26 is positioned within the cutout section 142 of the plate 130. A threaded screw 154 having a T-shaped handle 156 at one end and a flattened tip 158 at the other end is positioned within the throughbore 148 of the plate 130. When the threaded screw 154 is advanced within the throughbore 148 by turning the handle 156, the flattened tip 158 tightens against the foot brake housing 26 to prevent the base member 122 from pivoting about rod 152.

The circumferential guide 125 defines an arcuate path, which is the arc of a circle having a center, without the use of a pivoting radial member having one end at the center and the other end tracing the arcuate path. The preferred circumferential guide is an arcuate track 124 which comprises an arc of a circle and has an included angle of preferably 60°–70°. The length of the radius of the circle must be such that when the track is in one of its proper positions, the center of the circle is concentric with one of the hip locations. Other circumferential guides, such as bar linkages, which define an arcuate path without the use of a pivoting radial member may also be employed within the scope of the present invention.

Figure 17A:
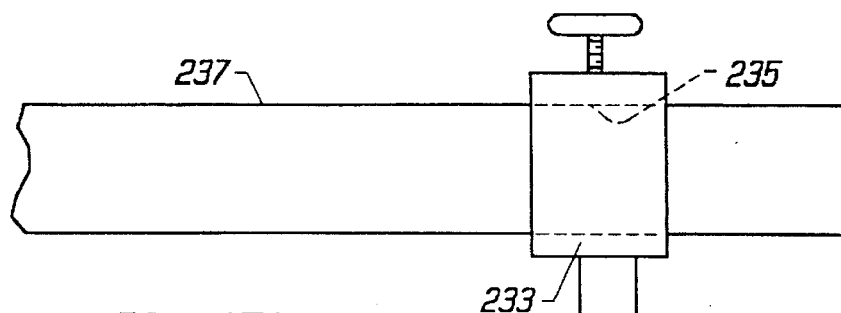
FIGS. 17A and 17B are a side view and a bottom view of the traction trolley of the traction system of FIG. 15.

As shown in FIG. 17A, the track is formed of a pair of identical parallel rafts 160, 162 each of which has a substantially square cross-section. Rail 160 is comprised of first walls 164a, 164b and second walls 166a, 166b. Rail 162 is comprised of first walls 168a, 168b and second walls 170a, 170b. A narrow plate 172 is attached to first walls 164b and 168a to connect the raft 160 to the rail 162.

Figure 18:
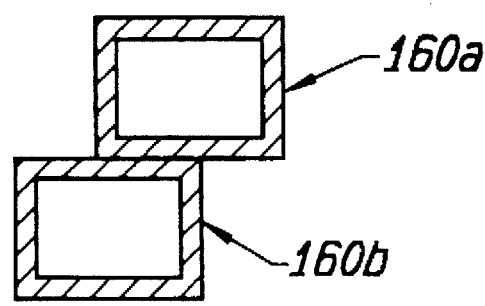
FIG. 18 is a cross-section view of an alternative arcuate track according to the present invention.

The arcuate track may be provided with any number of cross-sectional shapes. One alternative track cross-section, in which the rafts 160a, 160b are joined together in offset fashion, is shown in FIG. 18.

Figure 16A:
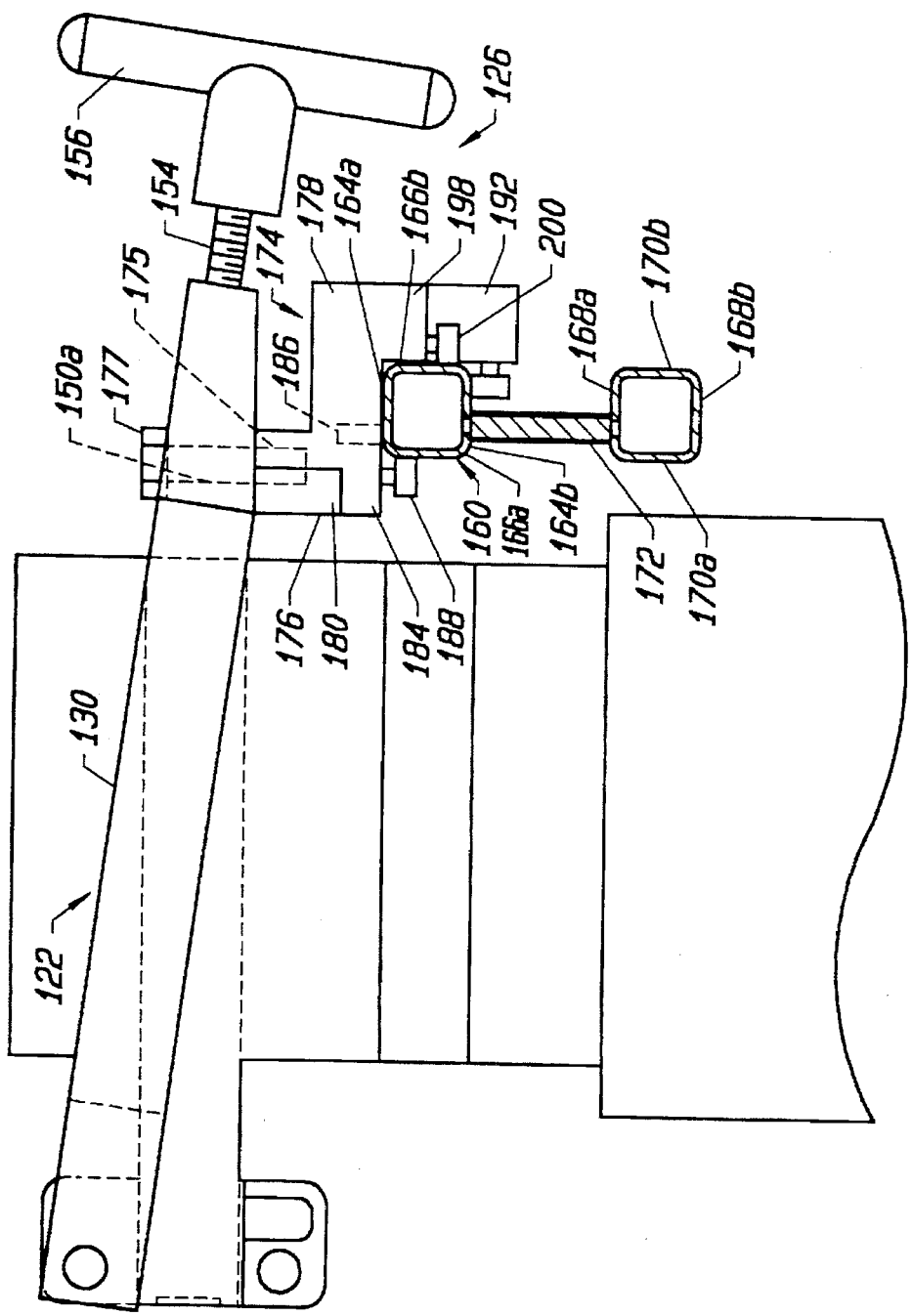
FIG. 16A is a side view of the base member of the traction system of FIG. 15 showing the configuration of the base trolley.
Figure 16B:
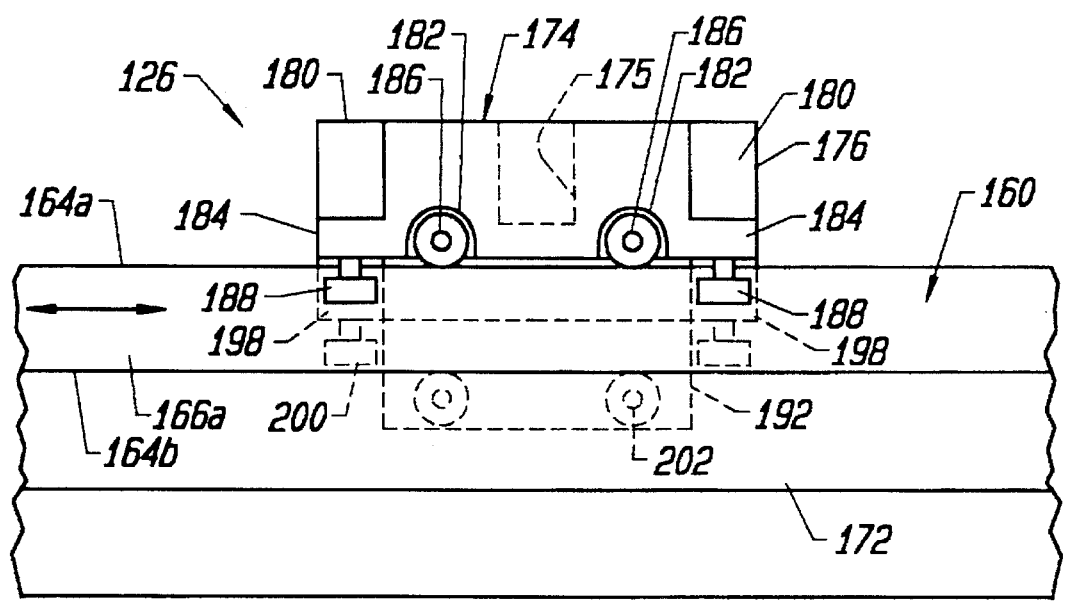
FIGS. 16B and 16C are a front elevation view and a rear elevation view, respectively, of the base trolley of FIG. 16A.
Figure 16C:
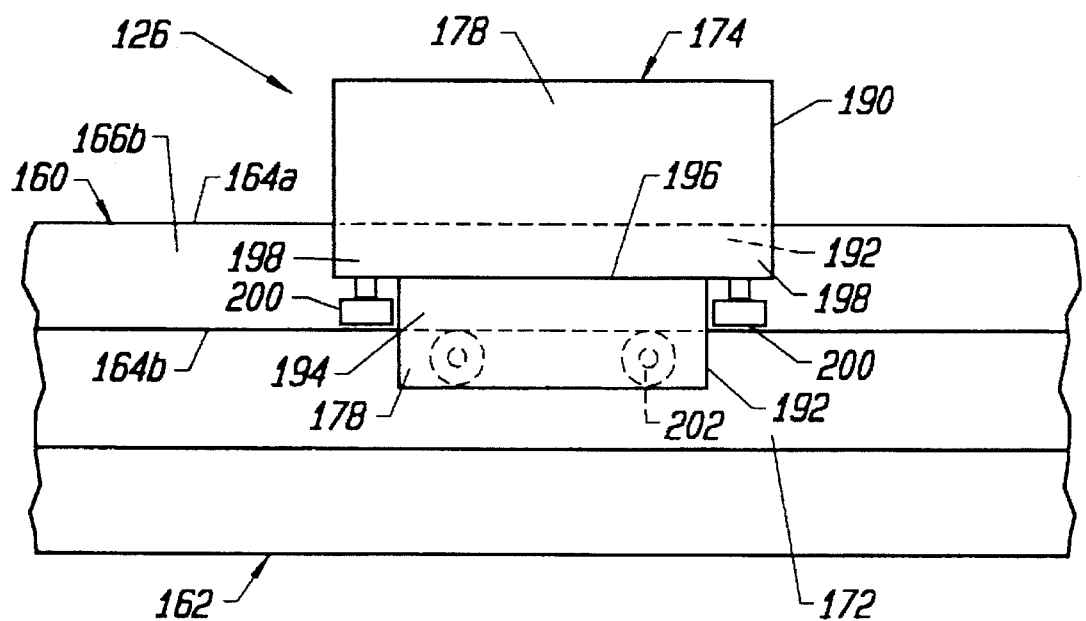

The base trolley 126 connects the arcuate track 124 to the base member 122 in the manner shown in FIG. 16A–16C. The base trolley is comprised of a plate 174 having a forward facing portion 176 and a rearward facing portion 178. The forward facing portion 176 is substantially rectangular and has a pair of rectangular recessed portions 180 and a pair of semi-circular recessed portions 182. Adjacent to each rectangular recessed portion 180 is a tab 184.

First rollers 186 are positioned in semi-circular recessed portions 182. Their axes of rotation are parallel to the wall 164a of rail 160 such that the rollers 186 roll along the wall 164a when the track 124 is moved in the directions indicated by arrows in FIGS. 16B and 16C. Second rollers 188 extend downwardly from the tabs 184 with their axes of rotation parallel to the face 166a of the track 124 such that the rollers 188 roll along face 166a when the track is moved in the directions indicated.

The rearward facing portion 178 is comprised of a first plate 190 and a second plate 192 secured to each other in partial overlapping relation. The second plate 192 extends from long side 196 of the first plate 190 such that portion 194 of the second plate does not overlap the first plate. The second plate 192 is centered along long side 196 such that side regions 198 of first plate 190 do not overlap with the second plate 192.

Third rollers 200 extend from side regions 198 of first plate 190 with their axes of rotation oriented to allow the rollers to roll along wall 166a of the rail 160 during movement of the track 124. Fourth rollers 202 are mounted to portion 194 of plate 192 with their axes of rotation extending normally of the plate 192 such that the rollers 202 roll along wall 164b of rail 160 during movement of the track 124.

A threaded bore 175 in plate 174 is proportioned for receiving a screw 177. The screw 177 is advanced through one of the bores 150a, 150b, 150c in the rectangular plate 130 to connect the base trolley 126 to the base member 122. Whether the base trolley 126 is connected to the base member 122 at bore 150a, bore 150b or bore 150c depends upon which leg is to be placed in traction. Proper operation of the traction table during abduction and traction requires that the hip of the leg to be placed in traction be concentric with the center of the circle defined by the arcuate track 124. The components of the traction unit are proportioned such that when the base trolley 126 is connected to the base member 122 at bore 150a, the center of the circle defined by the arcuate track 124 is hip location H1 (see FIG. 3), and when the base trolley 126 is connected to the base member 122 at bore 150b, the center of the circle defined by the arcuate track 124 is hip location H2. The hip locations H1 and H2 correspond to the center of rotation of each hip, which is the region wherein the femoral head rotates within the hip socket. Traction of both legs may be carried out by connecting the base trolley 126 to the base member 122 at bore 150c.

Figure 17B:
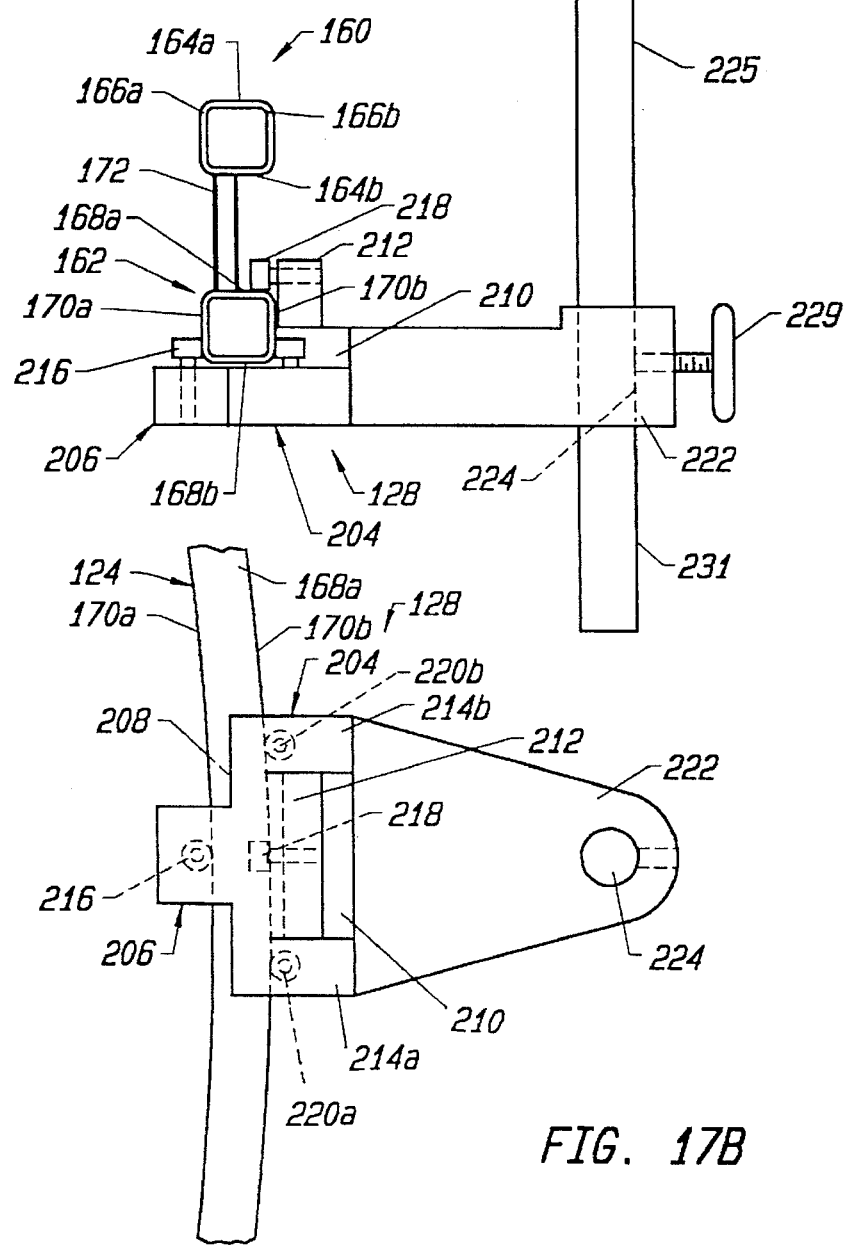

One of the traction trolleys 128 is shown in FIGS. 17A and 17B. The traction trolley 128 is comprised of a large rectangular plate 204 and a small rectangular plate 206 which is centered along long face 208 (see FIG. 17B) of the large rectangular plate 204.

Referring to FIG. 17A, the large rectangular plate 204 of the traction trolley 128 has a first elevated portion 210 and a second elevated portion 212 on top of the first elevated portion. A pair of side portions 214a, 214b, shown in FIG. 17B, are located on opposite sides of elevated portions 210 and 212.

A sixth roller 216 is positioned with its axis of rotation extending normally of small rectangular plate 206 such that it rolls on wall 170a of the rail 162 when the traction trolley 128 is moved along the track 124. A seventh roller 218 is mounted to second elevated portion 212 with its axis of rotation extending normally of the elevated portion 212 such that the roller can roll along wall 168a of the rail 162 during movement of the traction trolley 128. Eighth rollers 220a, 220b are mounted to the side portions 214a, 214b, respectively such that they roll along wall 170b of the rail 162 during movement of the traction trolley 128.

A base plate 222 having a throughbore 224 is mounted to the large rectangular plate 204. The throughbore 224 is for receiving a support rod 225 (FIG. 17A) for the traction unit 18 (not shown). A threaded screw 229 having a flattened end 231 is provided which may be tightened against the support rod 225 to prevent sliding of the rod within the throughbore 224 and to thereby lock the traction unit at a desired height.

A collar 233 is secured to support rod 225 and has a bore 235 which slidably receives member 237 of traction unit 18. The traction unit 18, which is not shown in detail, may be a conventional foot traction unit such as a Bell-type traction assembly.

Figure 19:
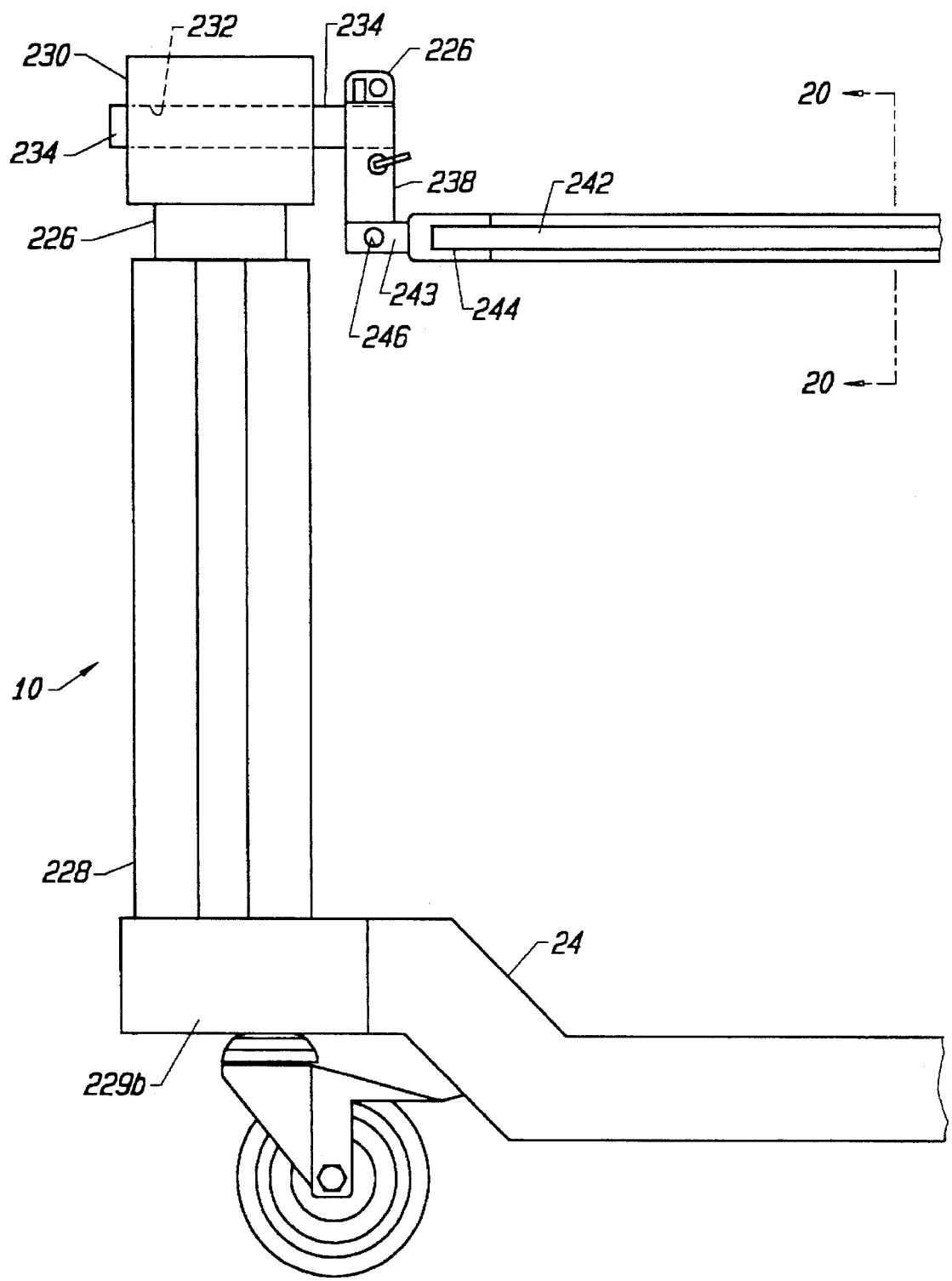
FIG. 19 is a side elevation view of the proximal end of the orthopedic table of FIG. 1.

Referring next to FIG. 19, the head post 10 is a substantially vertical post having a top section 226 slidably attached to bottom section 228 as described with respect to the foot post 12. A pair of wheel bases 229a, 229b (see FIG. 3) extend laterally from the bottom section 228, and the base beam 24 is connected to wheel base 229b.

Fixed to the top section 226 is a housing 230. A bore 232 having a longitudinal axis which is parallel to the longitudinal axis of the table passes through the housing 230. A shaft 234 is slidably and rotatably disposed within the bore 232. The housing may alternatively be mounted to a trolley similar to trolley 84 which slides relative to foot post 12. A braking device similar to braking device 104 may be provided for locking the shaft 234 against rotation.

A cross member 236 is fixed to one end of the shaft 234. The cross member 236 is an elongate member identical in construction to the cross member 32 associated with the foot post 12. Shaft 234 is fixed to the center of cross member 236.

A pair of parallel elongate members 238, 240 are suspended from the cross member 236 in a manner identical to that in which elongate members 48, 50 are suspended from cross member 32.

At the proximal end of the table, the patient support unit 14 is connected to the elongate members 238, 240. As shown in FIGS. 2 and 3, the patient support unit 14 is comprised of a substantially flat back board 242 having two parallel sides 241a, 241b and proximal and distal ends designated 244, 245, respectively. It is connected at its proximal end 244 to the elongate members 238, 240 by means of a mounting component 243 (FIG. 19). A bore 246 is formed in mounting component 243 and a rod 248, which may be locked into place, extends through the bore 246 and through one of the bores on each of the elongate members 238, 240.

Figure 20:
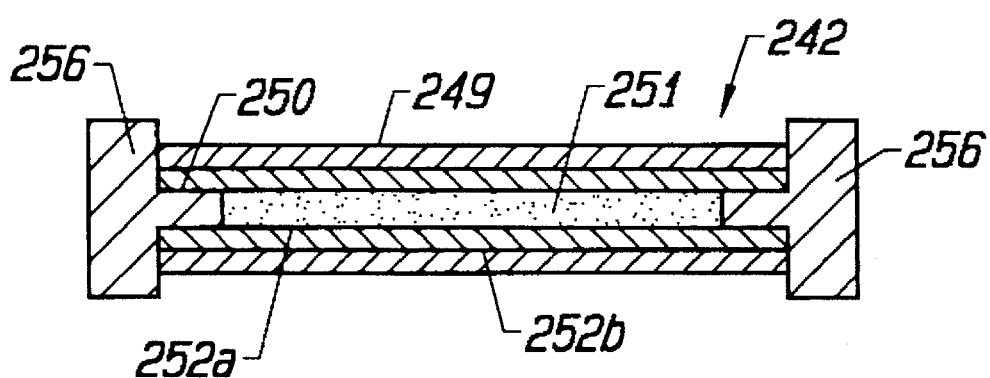
FIG. 20 is a cross-section view of the back board of the orthopedic table of FIG. 1 taken along the plane designated 20—20 in FIG. 19.

The board 242 is preferably constructed to have the cross-section shown in FIG. 20. The preferred board 242 is made from radiolucent materials to allow upper body imaging to be carried out on trauma patients suffering from multiple injuries and requiring lower limb traction. It is preferably formed of a top layer 249 of pionite, a second layer 250 of carbon fiber, a foam core 251, and a pair of carbon fiber lower layers 252a, 252b. Side pieces 256 are T-shaped members of carbon fiber composite material.

A dovetail connector 254 is attached to the distal end 245 of the board 242.

The base beam 24 of the table is configured such that it will provide support and balance to the table while using a minimum of floor space so that it will not obstruct positioning of an imaging intensification unit. Because the preferred table is intended to be used during imaging of both the lower limbs and the upper limbs and torso, the preferred base beam 24 design is positioned so that imaging may be easily carried out in these areas. It is comprised of an elongate member having three portions. The first portion 272 extends longitudinally from wheel base 229b near the head post 10 and passes underneath side 241b of patient board 242. The second portion 274 of the base beam 24 extends in angular relation to the first portion 272 towards the vertical plane of the longitudinal axis of the table. The third portion 276 is vertically aligned with the spar 66 and is connected to the bottom 22 of foot post 12. Configuring the base beam in this way avoids spreading the base of the table across the floor in the region between the sacral rest 258 and the traction unit 18 and thereby prevents it from becoming a substantial obstacle to the positioning of an image intensifier unit around a leg in traction.

Figure 21:
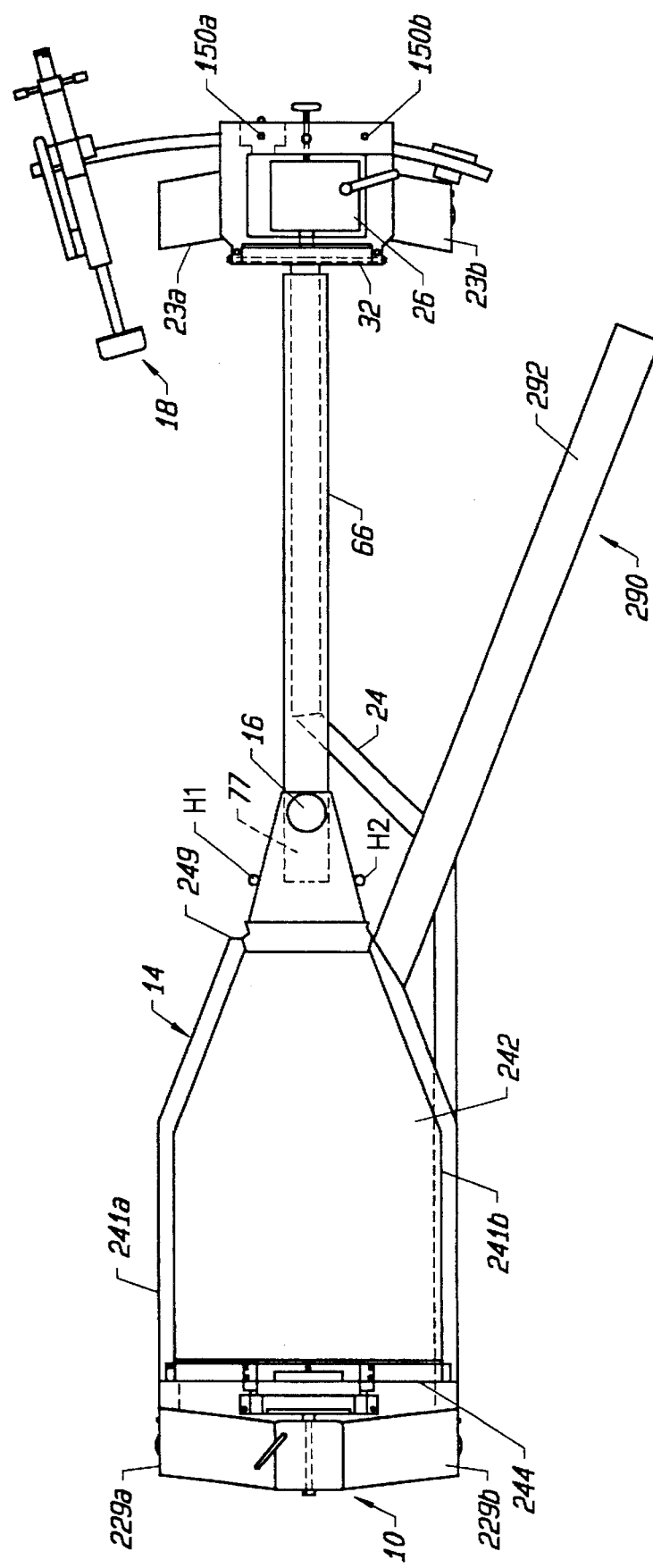
FIGS. 21 is a top plan view of an orthopedic table of the type shown in FIG. 1 and having a supplemental traction spar.

The table of the present invention may be provided with a supplemental traction spar, designated 290 in FIGS. 21 and 22. The supplemental spar may be used when it is desired to place both legs in traction at one time. It is comprised of an elongate spar 292 constructed of substantially radiolucent material, such as carbon fiber, and is preferably constructed to have a cross-section such as the one shown in FIG. 8. The elongate spar 292 is connected to the table by means of a table adaptor 288 secured around vertical portion 67 at the proximal end of the table spar 66 (see FIG. 1).

The table adaptor 288, which is shown isolated from the table in FIG. 22, has a substantially trapezoidal shape comprised of parallel walls 294, 296 and angled walls 298, 300 extending between the parallel sides. The walls surround a trapezoidal opening 302 through which the connector 68 (not shown) extends. Slots 304, 306 are formed in the angled walls 298, 300, respectively.

The elongate spar 292 has a proximal end 308 and a distal end 310. A traction unit (not shown), such as the traction unit 18 described above, is connected near the distal end 310 of the elongate spar 292. The proximal end 308 of the elongate spar 292 is formed into a finger 312 which is coupled to a spar connector 314.

The spar connector 314 is comprised of a block 316 having a pair of parallel walls 317a, 317b connected by perpendicular wall 319 and positioned on opposite sides of a rectangular notch 318 which receives the finger 312 as shown in FIG. 22. A threaded pin 320 is fixed to wall 317a and passes through notch 320, finger 312, and wall 317b. The spar 292 is pivotable around the pin 320 but may be locked against pivotal movement by means of a handle 322 having a threaded bore (not shown) which receives the threaded pin 320 and which, when tightened, presses the wall 317b, finger 312 and wall 317a together.

A coupling member 322 proportioned for sliding engagement with the slots 304, 306 on the table adaptor 288 is mounted to the wall 319. The elongate spar 292 may be selectively connected to either of the slots 304, 306, to provide traction for either of the patient's legs.

Operation

Figure 24:
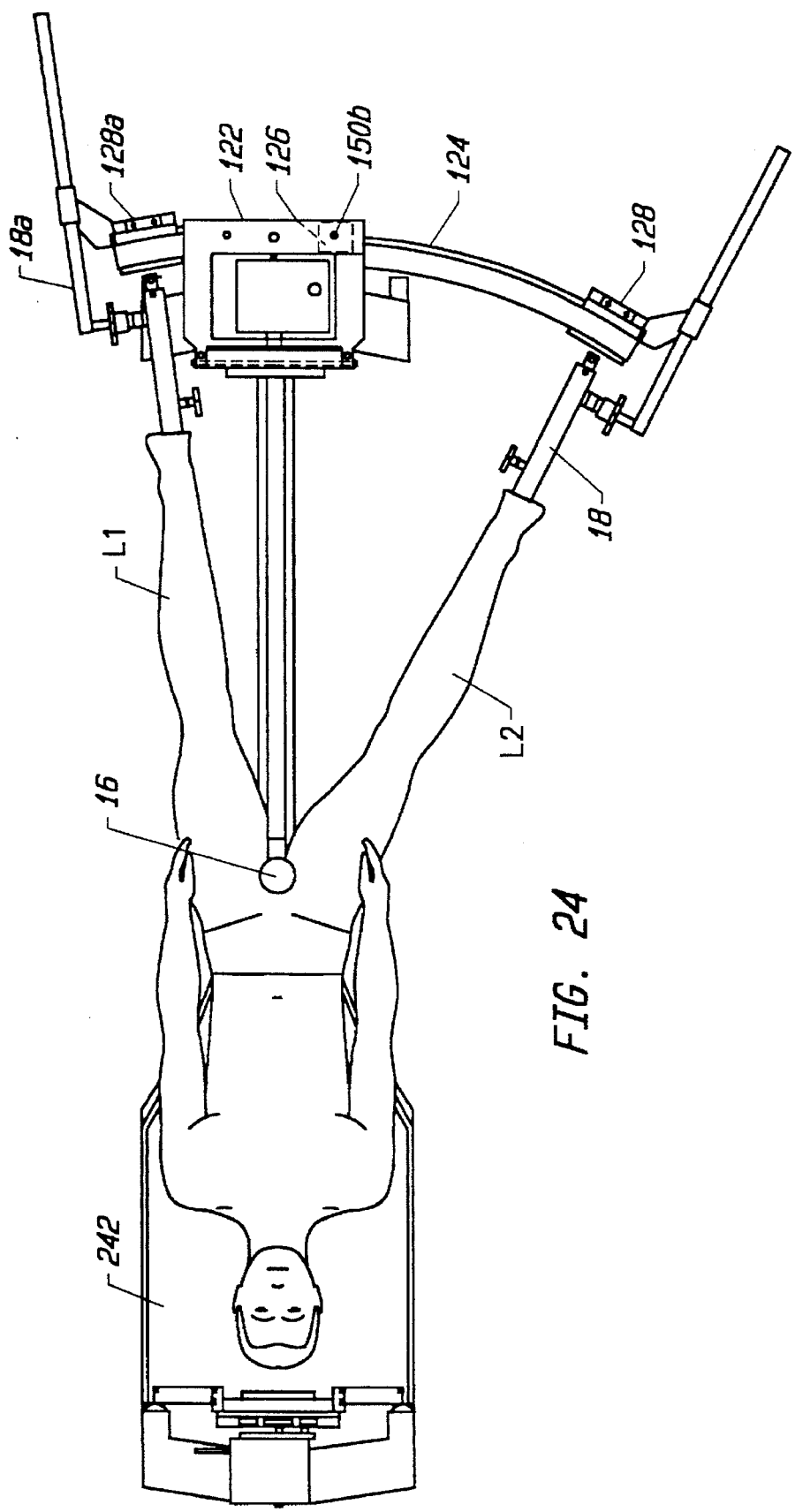
FIGS. 24 and 25 are of top plan views of the orthopedic table of FIG. 1 showing the use of the traction system according to the present invention.
Figure 25:
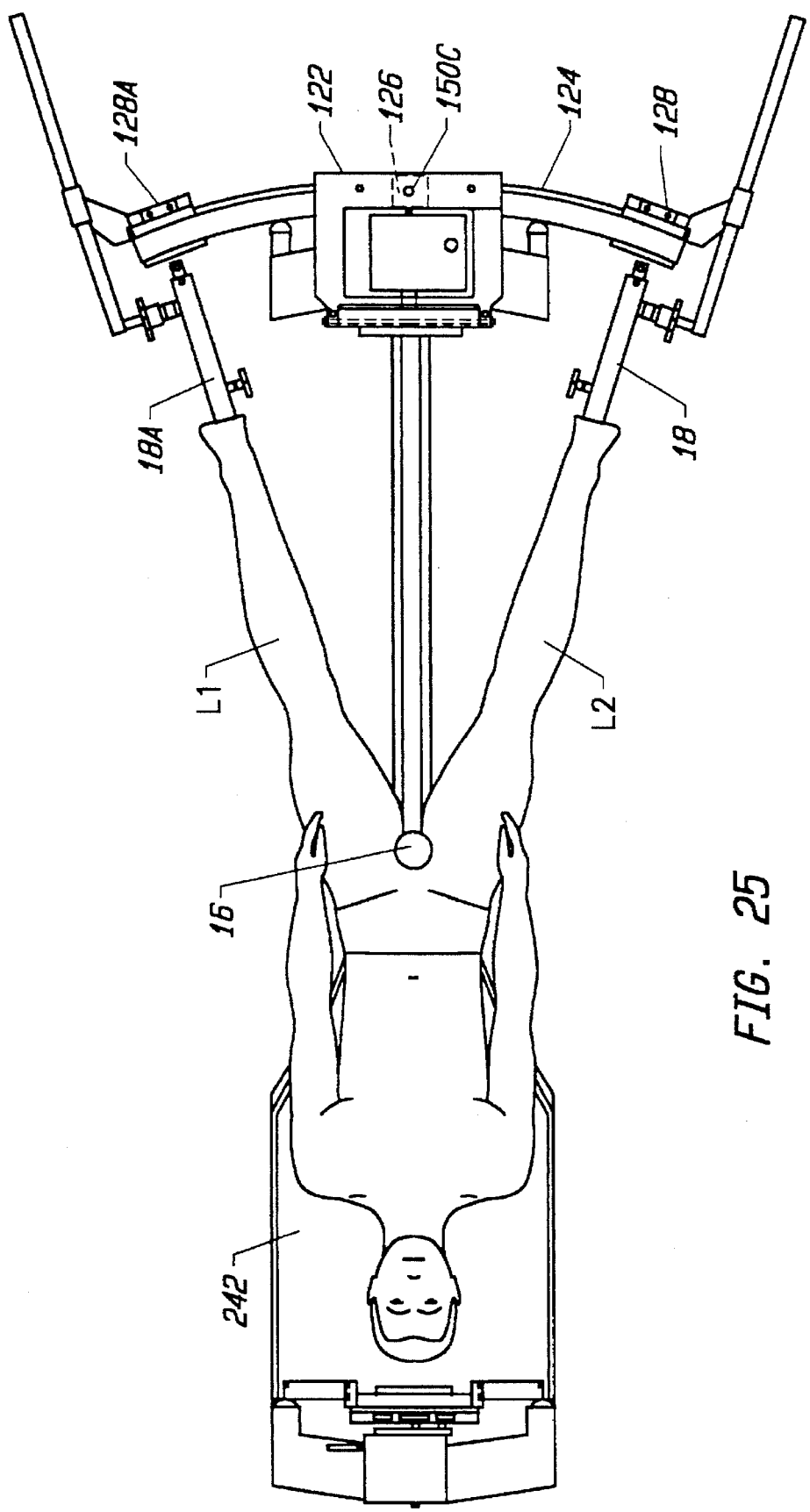

FIGS. 24 and 25 illustrate use of the apparatus of the present invention.

To place a patient's leg in traction for procedures requiring supinal positioning of the patient, the patient is placed on the patient support board 242 with its sacral region positioned on the supinal sacral rest 258 (see FIGS. 1 and 2). The perineal post 16 is positioned between the patients legs and the patient's hips positioned such that their centers of rotation are at the hip locations designated H1 and H2 in FIG. 3.

Assuming that it is desired to apply traction to leg L2, which has its hip center of rotation positioned at hip location H2, the base trolley 126 is secured to the base member 122 at bore 150b. Doing so orients the arcuate track 124 such that its center is concentric with hip location H2. Circumferential movement of the arcuate track 124, or of the traction unit 18 along the track, will thus have its center of motion at H2.

The arcuate track 124 may next be advanced circumferentially by sliding it along the needle bearing rollers provided in the base trolley 126. Advancing the arcuate track 124 to increase the mount of the rail on one side of the foot post 12 increases the angle through which the leg on that side of the foot post may be abducted. Once the arcuate track 124 is in a desired position, it is locked against the base trolley.

The foot traction unit 18 is next coupled to member 225 (see FIG. 17A) extending from the traction trolley which is on the side of the arcuate track 124 corresponding to leg L2. The traction trolley 128 is then moved circumferentially along the arcuate track 124 to position the traction unit 18 at a desired location for the procedure to be performed. The traction trolley 128 is then locked against the arcuate track to prevent unintended movement. The patient's foot is secured to the traction unit 18 and a traction force is applied through conventional use of the traction unit 18. If abduction or adduction is required after the traction force has been applied, the traction trolley 128 may be released from its locked position and advanced circumferentially along the arcuate track 124 until the desired degree of abduction or adduction has been achieved. The other leg L1 may be supported, with or without traction, by connecting it to traction unit 18a which is mounted to traction trolley 128a.

As shown in FIG. 25, by securing the base trolley 126 to the base member 122 at bore 150C, bilateral traction may be achieved with equal angles of abduction.

If desired, traction may be delivered to the other leg L1 by coupling it to a traction unit which is connected to the supplemental spar 290 (see FIG. 21). Coupling member 322 of the spar 290 is coupled to the table adaptor 288 at slot 306 (see FIG. 22), since that is the slot which is located on the same side of the table as leg L1. Abduction and adduction using the supplemental spar may be achieved by pivoting the spar member 292 around pivot pin 320 until the desired angle of abduction or adduction is reached, and by then locking the spar member into place by turning handle 322 into a tightened position.

As described above, x-ray images of the torso, upper body, and lower limbs may be carried out using an image intensification unit while the patient is positioned on the table.

If a hip spica cast is to be applied, the sacral rest may be removed from underneath the patient by sliding boards 260a, 260b (see FIGS. 1 and 12A) laterally in opposite directions such that they disengage from the dovetail connector 254 on the back support 242 and such that they allow the patient to drop slightly onto the casting saddle 77 (see FIG. 1, 2 and 23). The patient, and the casting saddle 77, are next wrapped with the casting material.

After the cast has been applied, the patient is lifted from the table with the casting saddle 77 still within the cast. As the patient is lifted, the sleeve 78 connected to the casting saddle 77 slides off column 74 and thus allows the casting saddle to be lifted from the table with the patient. The casting saddle is then removed from the cast.

Alternative Embodiment

As described above, in the preferred embodiment the arcuate track is the means which guides the traction device along an arcuate path the has a center of motion that is concentric with the patient's hip. It should be appreciated, however, that may alternate means may be implemented for guiding the traction device along such an arcuate path without the need for a radial member extending between the center of motion (i.e. the hip center) and the traction device.

For example, additional forms of arcuate tracks may be used to guide the traction unit. The traction unit may alternatively be coupled to a computer controlled servo which is programed to move the traction unit along an arcuate path which is centered at the hip center of rotation.

As another, example, a system of bar linkages may be employed which pivot relative to one another to guide the traction device along an arcuate path. One example of such a system is shown in FIG. 26.

Figure 26:
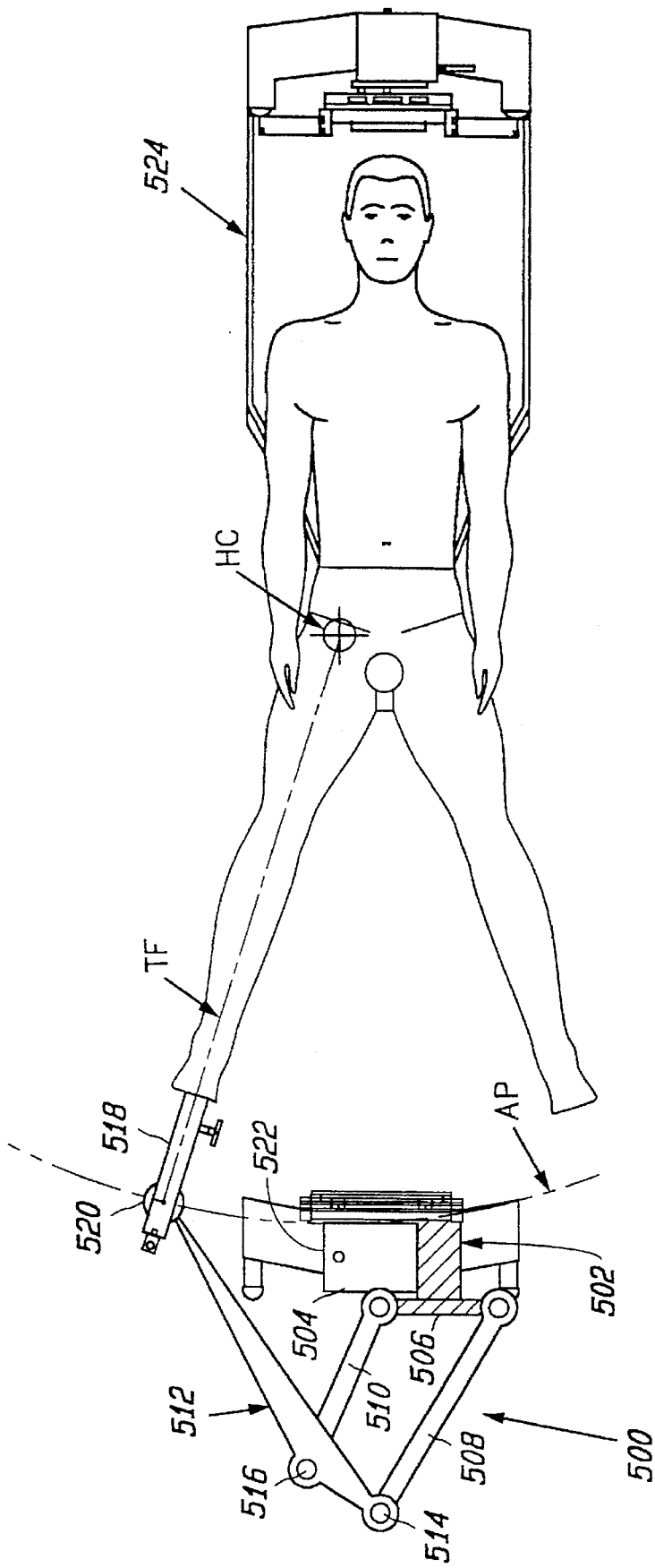
FIG. 26 is a top plan view of an alternative embodiment of a traction table in which a system of bar linkages is used for guiding the traction device in an arcuate path.

Referring to FIG. 26, the linkage system, designated generally as 500, is mounted by a base link 502 to the side of a housing 504 seated on top of a vertical column (which is similar to the column 12 of the preferred embodiment) at the foot end of the table.

The base link 502 is an approximately T-shaped member having a cross-piece 506. A first connector link 508 is pivotally attached to one end of cross-piece 506, and a second connector 510 is pivotally attached to the other end of cross-piece 506.

A triangular output link 512 is pivotally attached to first connector 508 at pivot point 514, attached to first connector 508 at pivot point 514, and is pivotally attached to second connector 510 at pivot point 516. A traction unit 518, which may be similar to the traction unit 18 of the preferred embodiment (see FIG. 1), is mounted at the free end, point 520, of output link 512 and is coupled to a patient's foot in a conventional manner.

The linkage system is coupled to post 504, which may be coupled to a traction table (see, for example, the manner in which post 10 is coupled to post 12 in the table in the embodiment of FIG. 1). Alternately, as shown in FIG. 26, the post 504 may be a stand-alone unit which is separate from the patient support table 524 (for example, the table may be of the conventional pedestal type) which supports the patient, and which is positioned at a location spaced from the table so that one or both of the patient's legs can be secured to the traction unit. As with the preferred embodiment, the patient's leg is coupled to the traction unit 518 to receive traction along traction force line TF.

By pivoting connector links 508, 510 relative to base link portion 506, the orientation of output link 512 may be modified such that free end 520, and thus the traction unit 518, travels about an arcuate path AP, which is centered at hip center HC. The links may be pivoted manually or by automatic means, and a locking means may be provided for locking the linkage into a desired orientation once the patient's leg has been moved to the desired angle of abduction or adduction.

The base link 502 is preferably detachably mountable to either side of the housing 504 so that traction can be applied to either leg. In other words, mounting the base link 502 as shown in FIG. 26 provides an arcuate path centered at hip center HC, which is concentric with the patient's fight hip. To apply traction to the patient's left hip, base link 502 would be removed from the housing 504 and re-attached at side 522 of the housing 504. The system may also be configured to utilize two linkage systems, one for the right leg and another for the left leg.

In the four bar linkage system described, the length of link 506 is preferably 12 inches, link 510 is preferably 14.78 inches in length, link 508 is preferably 20 inches in length, and the length of link 512 is preferably 6.58 inches. All of the above measurements are the center-to-center distances between the pivot points attached to the links. For example, the given length for link 512 is the center to center distance between pivots 514 and 516. Naturally, links of different lengths may be utilized, so long as they are calculated to move the traction unit 518 along an arcuate path such that the center of motion of the traction unit is centered at the hip location HC.

Other linkage systems, which utilize different numbers and configurations of linkages, may also be used without exceeding the scope of the present invention.

The present invention was described in relation to a preferred embodiment. However, it will be apparent to one skilled in the art that one can practice numerous alternative embodiments and still practice an invention within the spirit and scope of the present invention.

We claim:

1. A traction apparatus for use with a table of a type for supporting a human patient having a leg and further having a hip with a center of rotation, the apparatus for applying traction to a leg of a such a human patient positioned on such a table, comprising, in combination:

stabilizing means for attachment to a table and, when the stabilizing means is attached to a table and a patient is positioned on the table, for at least partially securing the patient against the table so as to restrict movement of a hip of the patient relative to the table;

traction means for coupling to a leg of a patient positioned on a table and for applying a traction force to the leg to place the leg in tension while the stabilizing means restricts movement of the patient's hip relative to the table; and guide means for guiding the traction means along an arcuate path such that when a patient is positioned on a table with the traction means coupled to a leg of the patient, the traction means is moveable along the arcuate path about a center of motion that is concentric with the hip of the patient and that is spatially and operatively remote from the traction means.

2. The apparatus of claim 1 wherein the apparatus is further for use on a table of the type having proximal and distal ends and wherein:

the guide means comprises an arcuate rail having a center of curvature, the traction means being coupled to the rail for slidable movement along the rail, with the center of movement of the traction means corresponding to the center of curvature of the rail, the rail mountable to a distal end of a table.

3. The apparatus of claim 2 wherein the arcuate rail is slidable in a circumferential direction such that its center of curvature remains concentric with the hip location.

4. The apparatus of claim 2 wherein the traction means is coupled to a traction trolley, the traction trolley slidable along the rail in a circumferential direction, such that its center of motion is concentric with the hip location, to position the traction device in a desired traction position.

5. The apparatus of claim 1 wherein the components are further for use with a table of the type having proximal and distal ends and a patient support board which is connected to the proximal end of the table and which has proximal and distal sections and wherein:

the stabilizing means includes a perineal post extendable from a distal section of a patient support board of a table and proportioned for applying countertraction at a perineal region of a patient positioned on a patient support board to which the perineal post is attached.

6. In a table for use in applying a cast to a patient having legs, the table of the type having a patient support board for supporting the patient, a stabilizing device for securing the patient on the patient support board, and a traction unit for applying traction to at least one of the legs, the improvement comprising:

a sacral support board mountable in lateral sliding engagement to a distal section of a patient support board and proportioned for supporting a sacral region of the patient;

a casting saddle having a plate attached to support means for coupling to the table and for supporting the plate below the sacral support board, the plate proportioned to receive the sacral region of the patient when the sacral support board is slidably detached from the patient support board.

7. The apparatus of claim 6 wherein the sacral support board is comprised of first and second pieces oriented in side by side relationship such that each piece is mountable in lateral sliding engagement to a portion of the distal section of a patient support board.

8. A table for supporting a patient having a leg and a hip with a center of rotation, the table further for delivering traction to a leg of such a patient, the apparatus comprising:

a proximal support member and a distal support member positioned in spaced relationship;

a base member extending between the proximal and distal support members;

a patient support board extending from the proximal support member towards the distal support member;

stabilizing means for, when a patient is positioned on the table, at least partially securing the patient against the patient support board so as to restrict movement of a hip of the patient relative to the table;

traction means for coupling to a leg of a patient positioned on the patient support board and for applying a traction force to the leg while the stabilizing means restricts movement of the patient's hip relative to the table; and guide means for guiding the traction means along an arcuate path such that when a patient is positioned on the patient support board with the traction means coupled to a leg of the patient, the traction means is moveable along the arcuate path about a center of motion that is concentric with the patient's hip and that is spatially and operatively remote from the traction means.

9. The apparatus of claim 8 wherein:

the traction means includes an arcuate rail having a center of curvature, the arcuate rail coupled to the distal support member such that when a patient is positioned on a table with the traction means coupled to a leg of the patient, the center of curvature of the arcuate rail is concentric with a center of rotation of the patient's hip, the traction means further including a traction device coupled to the rail for slidable movement along the rail with the center of movement of the traction means corresponding to the center of curvature of the rail.

10. The apparatus of claim 9 wherein the arcuate rail is slidable in a circumferential direction relative to the distal support member such that its center of curvature remains concentric with the hip location.

11. The apparatus of claim 9 wherein the traction device is coupled to a traction trolley, the traction trolley slidable along the rail in a circumferential direction such that its center of motion is concentric with the hip location to position the traction device in a desired traction position.

12. The apparatus of claim 8 wherein:

the patient support board has a proximal section coupled to the proximal support member and a distal section extending towards the distal support member; and the stabilizing means further comprises a sacral support board proportioned to support the sacral region of a patient's back and having a proximal portion mounted in lateral sliding engagement to the distal section of the patient support board.

13. The apparatus of claim 12 wherein the apparatus further comprises a casting saddle having a plate attached to support means for coupling the plate to the patient support board and for supporting the plate below the sacral support board, the plate proportioned to receive a sacral region of the patient when the sacral support board is slidably detached from the patient support board.

14. The apparatus of claim 12 wherein the sacral support board is comprised of first and second pieces oriented in side by side relationship such that each piece is mounted in lateral sliding engagement to a portion of the distal section of the patient support board.

15. The apparatus of claim 14 wherein the apparatus further comprises a casting saddle having a plate attached to support means for coupling the plate to the patient support board and for supporting the plate below the sacral support board, the plate proportioned to receive a sacral region of the patient when the first and second pieces of the sacral support board are slidably detached from the patient support board.

16. The apparatus of claim 8 wherein the patient support board is constructed of substantially radiolucent material.

17. The apparatus of claim 8 wherein the patient support board has a longitudinal axis located within a vertical plane and wherein the base member has a proximal section spaced from the vertical plane.

18. The apparatus of claim 17 wherein the patient support board has a distal section, wherein a table spar extends longitudinally between the distal section of the patient support board and the distal support member.

19. The apparatus of claim 18 wherein the table spar is constructed of substantially radiolucent material.

20. In a table for providing traction to a leg of a patient wherein the table is of the type having a board for supporting the patient, a spar pivotally mounted to the table and a traction unit connected to the spar, and wherein the table is of the type used for supporting the patient during x-ray imaging procedures, the improved spar comprising:

an elongate member comprised of a plurality of elongate walls, each wall connected between two of the other walls to form a tubular member and each wall having an orientation selected from the group of orientations consisting of orientations that are normal or oblique to x-rays directed towards the spar during the x-ray imaging procedures.

21. The apparatus of claim 20 wherein the spar is comprised of four elongate walls joined in angular relation such that the spar has a cross-section that is trapezoidal in shape.

22. The apparatus of claim 20 wherein the spar is comprised of six elongate walls in angular relation such that the spar has a cross-section that is hexagonal in shape.

23. In a table for supporting a patient during x-ray procedures wherein the table is of the type having a first end, a second end, a patient support device extending from the first end towards the second end, and a table spar extending between the patient support device and the second end of the table, the improved table spar comprising:

an elongate member comprised of a plurality of elongate walls, each wall connected between two of the other walls to form a tubular member and each wall having an orientation selected from the group of orientations consisting of orientations that are normal or oblique to x-rays directed towards the spar during the x-ray imaging procedures.

24. The apparatus of claim 23 wherein the spar is comprised of four elongate walls joined in angular relation such that the spar has a cross-section that is trapezoidal in shape.

25. The apparatus of claim 23 wherein the spar is comprised of six elongate walls in angular relation such that the spar has a cross-section that is hexagonal in shape.

26. An apparatus for applying traction to a leg of a patient having a leg and a hip when the patient is positioned on a table having a table surface and when the patient is secured to the table in a manner which restricts movement of a hip of the patient, the apparatus comprising:

a base;

traction means for coupling to a leg of a patient positioned on a table surface near the base and for applying a tensile force to a leg of a patient while the patient is secured to the table in a manner which restricts movement of the patient's hip; and guide means for guiding the traction means along an arcuate path such that when a patient is positioned on a table surface adjacent to the base and the traction means is coupled to a leg of the patient, the traction means is moveable along the arcuate path about a center of motion that is concentric with the patient's hip and that is spatially operatively remote from the traction means.

27. An apparatus for applying traction to a leg of a patient having a leg and a hip when the patient is positioned on a table having a table surface and when the patient is secured to the table in a manner which restricts movement of a hip of the patient, the apparatus comprising:

a base;

a plurality of linkages pivotally coupled to the base and to one another, at least one of the linkages having a free end, the linkages pivotable relative to one another to move the free end along an arcuate path; and traction means attached to the free end, for coupling to a leg of a patient positioned on a table surface near the base and for applying a tensile force to a leg of a patient while the patient is secured to the table in a manner which restricts movement of the patient's hip.

28. The improvement of claim 6 wherein the sacral support board is comprised of first and second pieces oriented in side by side relationship such that each piece is mounted in lateral sliding engagement to a portion of the distal section of the patient support board.

* * * * *